United States Patent [19]
Whittle et al.

[11] Patent Number: 5,955,087
[45] Date of Patent: Sep. 21, 1999

[54] POLYPEPTIDES USEFUL AS IMMUNOTHERAPEUTIC AGENTS AND METHODS OF POLYPEPTIDE PREPARATION

[75] Inventors: Nigel Richard Whittle, Cambridge; Jeremy Paddon Carmichael, Belfast; Stephen Edward Connor, Cambridge; Henry Stephen Grammer Thompson, Cambridge; Mark Jonathan Wilson, Cambridge, all of United Kingdom

[73] Assignee: Cantab Pharmaceuticals Research Limited, Cambridge, United Kingdom

[21] Appl. No.: 08/606,288

[22] Filed: Feb. 23, 1996

Related U.S. Application Data

[60] Provisional application No. 60/000,034, Jun. 8, 1995.

[30] Foreign Application Priority Data

Feb. 24, 1995 [GB] United Kingdom .................. 9503786
Jul. 28, 1995 [GB] United Kingdom .................. 9515478

[51] Int. Cl.$^6$ ............................ A61K 39/12; C12P 21/06; C07H 21/04
[52] U.S. Cl. .................. 424/204.1; 435/69.1; 435/235.1; 435/320.1; 530/350; 536/23.72; 536/23.4
[58] Field of Search .................. 435/69.3, 69.1, 435/235.1, 320.1; 530/350; 536/23.72, 23.4; 424/204.1

[56] References Cited

U.S. PATENT DOCUMENTS

| | | | |
|---|---|---|---|
| 4,766,224 | 8/1988 | Rausch | 530/412 |
| 5,618,536 | 4/1997 | Lowy et al. | 424/192.1 |

FOREIGN PATENT DOCUMENTS

| | | |
|---|---|---|
| 04 51550A2 | 3/1991 | European Pat. Off. |
| 04 56197A1 | 5/1991 | European Pat. Off. |
| 92 05248 | 4/1992 | WIPO |
| 92 16636A1 | 10/1992 | WIPO |
| 93 00436 | 1/1993 | WIPO |
| 93 20844 | 10/1993 | WIPO |
| 96 11274 | 4/1996 | WIPO |

OTHER PUBLICATIONS

Rose et al, J. of Virology, vol. 67, No. 4, pp. 1936–1944. Apr. 1993.

Pilacinski et al, 1986, Ciba Foundation Symposium 120, pp. 136–156.

Mandelson, et al., "The Association of Human Papillomavirus Antibodies with Cervical Cancer Risk", *Cancer Epidemiology Biomarkers & Prevention*, 1 (4) :281–286 (1992).

Koechel, et al., "Occurence of Antibodies to L1 L2 E4 and E7 Gene Products of Human Papillomavirus Types 6B 16 and 18 Among Cervical Cancer Patients and Controls", *Int. J. Cancer*, 48 (5) :682–688 (1991).

Crum, et al., "Coexpression of the Human Papillomavirus Type 16 E4 and L1 Open Reading Frames in Early Cervical Neoplasia", *Virology*, 178:238–246 (1990).

Pilacinski et al., Cloning and expression in *E. coli* of the bovine papillomavirus L1 and L2 open reading frames. Biotechnology Apr. 1984 p. 356–360.

Köchel et al. Antibodies to human papillomavirus type–16 in human sera as revealed by the use of prokayotically expressed viral gene products. Virology 182: 644–654 (1991).

*Primary Examiner*—Mary E. Mosher
*Assistant Examiner*—Ali R. Salimi
*Attorney, Agent, or Firm*—Klarquist Sparkman Campbell Leigh & Whinston, LLP

[57] ABSTRACT

Fusion polypeptides and aggregates of polypeptides comprising papillomavirus-derived antigens, and compositions thereof and their use e.g. with adjuvants for immunogenic and vaccine purposes in eliciting e.g. HPV-specific immune responses. The polypeptides can be purified to result in aggregates which when in solution or dispersion can pass through a sterilisation filter, and in amorphous aggregates. An example of such a polypeptide is a fusion protein of human papillomavirus proteins L2 and E7.

15 Claims, 8 Drawing Sheets

FIG. 1A

```
ATACAT ATG AAA TAC CTG CTG CCG ACC GCT GCT GCT GGT CTG CTG CTC    48
       Met Lys Tyr Leu Leu Pro Thr Ala Ala Ala Gly Leu Leu Leu
        1               5                  10
CTC GCT GCC CAG CCG GCG ATG GCC ATG GAT ATC GGA ATT AAT TCG GAT   96
Leu Ala Ala Gln Pro Ala Met Ala Met Asp Ile Gly Ile Asn Ser Asp
 15              20                  25                      30
CTG GCA CAT AGT AGG GCC CGA CGA CGC AAG CGT GCG TCA GCT ACA CAG  144
Leu Ala His Ser Arg Ala Arg Arg Arg Lys Arg Ala Ser Ala Thr Gln
                 35                  40                  45
CTA TAT CAA ACA TGT AAA CTC ACT GGA ACA TGC CCC CCA GAT GTA ATT  192
Leu Tyr Gln Thr Cys Lys Leu Thr Gly Thr Cys Pro Pro Asp Val Ile
             50                  55                  60
CCT AAG GTG GAA CAC AAC ACC ATT GCA GAT CAA ATA TTA AAA TGG GGG  240
Pro Lys Val Glu His Asn Thr Ile Ala Asp Gln Ile Leu Lys Trp Gly
         65                  70                  75
AGT TTG GGG GTG TTC TTC GGA GGG TTG GGT ATA GGC ACC GGT TCC GGC  288
Ser Leu Gly Val Phe Phe Gly Gly Leu Gly Ile Gly Thr Gly Ser Gly
         80              85                  90
ACT GGG GGT CGT ACT GGC TAT GTT CCC TTA GGA ACT TCT GCA AAA CCT  336
Thr Gly Gly Arg Thr Gly Tyr Val Pro Leu Gly Thr Ser Ala Lys Pro
 95             100                 105                     110
TCT ATT ACT AGT GGG CCT ATG GCT CGT CCT CCT GTG GTG GTG GAG CCT  384
Ser Ile Thr Ser Gly Pro Met Ala Arg Pro Pro Val Val Val Glu Pro
                115                 120                 125
GTG GCC CCT TCG GAT CCA TCC ATT GTG TCT TTA ATT GAA GAA TCG GCA  432
Val Ala Pro Ser Asp Pro Ser Ile Val Ser Leu Ile Glu Glu Ser Ala
            130                 135                 140
ATC ATT AAC GCA GGG GCG CCT GAA ATT GTG CCC CCT GCA CAC GGT GGG  480
Ile Ile Asn Ala Gly Ala Pro Glu Ile Val Pro Pro Ala His Gly Gly
        145                 150                 155
TTT ACA ATT ACA TCC TCT GAA ACA ACT ACC CCT GCA ATA TTG GAT GTA  528
Phe Thr Ile Thr Ser Ser Glu Thr Thr Thr Pro Ala Ile Leu Asp Val
    160                 165                 170
TCA GTT ACT AGT CAT ACT ACT ACT AGT ATA TTT AGA AAT CCT GTC TTT  576
Ser Val Thr Ser His Thr Thr Thr Ser Ile Phe Arg Asn Pro Val Phe
175                 180                 185                 190
```

FIG. 1B

```
ACA GAA CCT TCT GTA ACA CAA CCC CAA CCA CCC GTG GAG GCT AAT GGA    624
Thr Glu Pro Ser Val Thr Gln Pro Gln Pro Pro Val Glu Ala Asn Gly
            195                 200                 205
CAT ATA TTA ATT TCT GCA CCC ACT ATA ACG TCA CAC CCT ATA GAG GAA    672
His Ile Leu Ile Ser Ala Pro Thr Ile Thr Ser His Pro Ile Glu Glu
            210                 215                 220
ATT CCT TTA GAT ACT TTT GTG ATA TCC TCT AGT GAT AGC GGT CCT ACA    720
Ile Pro Leu Asp Thr Phe Val Ile Ser Ser Ser Asp Ser Gly Pro Thr
            225                 230                 235
TCC AGT ACC CCT GTT CCT GGT ACT GCA CCT CGG CCT CGT GTG GGC CTA    768
Ser Ser Thr Pro Val Pro Gly Thr Ala Pro Arg Pro Arg Val Gly Leu
            240                 245                 250
TAT AGT CGT GCA TTG CAC CAG GTG CAG GTT ACA GAC CCT GCA TTT CTT    816
Tyr Ser Arg Ala Leu His Gln Val Gln Val Thr Asp Pro Ala Phe Leu
255                 260                 265                 270
TCC ACT CCT CAA CGC TTA ATT ACA TAT GAT AAC CCT GTA TAT GAA GGG    864
Ser Thr Pro Gln Arg Leu Ile Thr Tyr Asp Asn Pro Val Tyr Glu Gly
            275                 280                 285
GAG GAT GTT AGT GTA CAA TTT AGT CAT GAT TCT ATA CAC AAT GCA CCT    912
Glu Asp Val Ser Val Gln Phe Ser His Asp Ser Ile His Asn Ala Pro
            290                 295                 300
GAT GAG GCT TTT ATG GAC ATA ATT CGT TTG CAC AGA CCT GCT ATT GCG    960
Asp Glu Ala Phe Met Asp Ile Ile Arg Leu His Arg Pro Ala Ile Ala
            305                 310                 315
TCC CGA CGT GGC CTT GTG CGG TAC AGT CGC ATT GGA CAA CGG GGG TCT   1008
Ser Arg Arg Gly Leu Val Arg Tyr Ser Arg Ile Gly Gln Arg Gly Ser
            320                 325                 330
ATG CAC ACT CGC AGC GGA AAG CAC ATA GGG GCC CGC ATT CAT TAT TTT   1056
Met His Thr Arg Ser Gly Lys His Ile Gly Ala Arg Ile His Tyr Phe
335                 340                 345                 350
TAT GAT ATT TCA CCT ATT GCA CAA GCT GCA GAA GAA ATA GAA ATG CAC   1104
Tyr Asp Ile Ser Pro Ile Ala Gln Ala Ala Glu Glu Ile Glu Met His
            355                 360                 365
CCT CTT GTG GCT GCA CAG GAA GAT ACA TTT GAT ATT TAT GCT AAA TCT   1152
Pro Leu Val Ala Ala Gln Glu Asp Thr Phe Asp Ile Tyr Ala Lys Ser
            370                 375                 380
```

FIG. 1C

```
TTT GAA CCT GAC ATT AAC CCT ACC CAA CAC CCT GTT ACA AAT ATA TCA    1200
Phe Glu Pro Asp Ile Asn Pro Thr Gln His Pro Val Thr Asn Ile Ser
        385                 390                 395
GAT ACA TAT TTA ACT TCC ACA CCT AAT ACA GTT ACA CAA CCG TGG GGT    1248
Asp Thr Tyr Leu Thr Ser Thr Pro Asn Thr Val Thr Gln Pro Trp Gly
    400                 405                 410
AAC ACC ACA GTT CCA TTG TCA ATT CCT AAT GAC CTG TTT TTA CAG TCT    1296
Asn Thr Thr Val Pro Leu Ser Ile Pro Asn Asp Leu Phe Leu Gln Ser
415                 420                 425                 430
GGC CCT GAT ATA ACT TTT CCT ACT GCA CCT ATG GGA ACA CCC TTT AGT    1344
Gly Pro Asp Ile Thr Phe Pro Thr Ala Pro Met Gly Thr Pro Phe Ser
            435                 440                 445
CCT GTA ACT CCT GCT TTA CCT ACA GGC CCT GTT TTC ATT ACA GGT TCT    1392
Pro Val Thr Pro Ala Leu Pro Thr Gly Pro Val Phe Ile Thr Gly Ser
        450                 455                 460
GGA TTT TAT TTG CAT CCT GCA TGG TAT TTT GCA CGT AAA CGC CGT AAA    1440
Gly Phe Tyr Leu His Pro Ala Trp Tyr Phe Ala Arg Lys Arg Arg Lys
    465                 470                 475
CGT ATT CCC TTA TTC TTC TCA GAT GTG GCG GCC TCC ATG GCG ATG CAT    1488
Arg Ile Pro Leu Phe Phe Ser Asp Val Ala Ala Ser Met Ala Met His
480                 485                 490
GGA AGA CAT GTT ACC CTA AAG GAT ATT GTA TTA GAC CTG CAA CCT CCA    1536
Gly Arg His Val Thr Leu Lys Asp Ile Val Leu Asp Leu Gln Pro Pro
495                 500                 505                 510
GAC CCT GTA GGG TTA CAT TGC TAT GAG CAA TTA GTA GAC AGC TCA GAA    1584
Asp Pro Val Gly Leu His Cys Tyr Glu Gln Leu Val Asp Ser Ser Glu
            515                 520                 525
GAT GAG GTG GAC GAA GTG GAC GGA CAA GAT TCA CAA CCT TTA AAA CAA    1632
Asp Glu Val Asp Glu Val Asp Gly Gln Asp Ser Gln Pro Leu Lys Gln
        530                 535                 540
CAT TAC CAA ATA GTG ACC TGT TGC TGT GGA TGT GAC AGC AAC GTT CGA    1680
His Tyr Gln Ile Val Thr Cys Cys Cys Gly Cys Asp Ser Asn Val Arg
    545                 550                 555
CTG GTT GTG CAG TGT ACA GAA ACA GAC ATC AGA GAA GTG CAA CAG CTT    1728
Leu Val Val Gln Cys Thr Glu Thr Asp Ile Arg Glu Val Gln Gln Leu
560                 565                 570
```

FIG. 1D

```
CTG TTG GGA ACA CTA AAC ATA GTG TGT CCC ATC TGC GCA CCG AAG ACC   1776
Leu Leu Gly Thr Leu Asn Ile Val Cys Pro Ile Cys Ala Pro Lys Thr
575             580             585             590
GCG GCC GCA CTC GAG CAC CAC CAC CAC CAC CAC TGA GAT               1815
Ala Ala Ala Leu Glu His His His His His His *
                595             600 601
```

FIG. 1E

```
T7 Promoter, Lac Operator and rbs regions preceding start codon
AGATCTCGATCCCGCGAAAT TAATACGACTCACTATAGGG GAATTGTGAGCGGATAACAA
1                    20                   40                   60
TTCCCCTCTAGAAATAATTT TGTTTAACTTTAAGAAGGAG AT   ATACAT
                     80                   100      108
```

FIG. 1F

```
T7 Terminator sequence
GAT CCGGCTGCTAACAAAGC CCGAAAGGAAGCTGAGTTGG CTGCTGCCACCGCTGAGCAA
1                     20                   40                   60
TAACTAGCATAACCCCTTGG GGCCTCTAAACGGGTCTTGA GGGGTTTTTTG
                     80                   100         111
```

FIG. 2A

| | | | | | | | | | | | | | | |
|---|---|---|---|---|---|---|---|---|---|---|---|---|---|---|
|Met|Lys|Tyr|Leu|Leu|Pro|Thr|Ala|Ala|Ala|Gly|Leu|Leu|Leu|Ala|
|1| | | |5| | | | |10| | | | |15|

Ala Gln Pro Ala Met Ala Met Asp Ile Gly Ile Asn Ser Asp Leu Ala
              20            25                  30

His Ser Arg Ala Arg Arg Arg Lys Arg Ala Ser Ala Thr Gln Leu Tyr
            35              40                  45

Gln Thr Cys Lys Leu Thr Gly Thr Cys Pro Pro Asp Val Ile Pro Lys
        50              55              60

Val Glu His Asn Thr Ile Ala Asp Gln Ile Leu Lys Trp Gly Ser Leu
65              70                  75                      80

Gly Val Phe Phe Gly Gly Leu Gly Ile Gly Thr Gly Ser Gly Thr Gly
                85                  90                  95

Gly Arg Thr Gly Tyr Val Pro Leu Gly Thr Ser Ala Lys Pro Ser Ile
            100             105             110

Thr Ser Gly Pro Met Ala Arg Pro Pro Val Val Val Glu Pro Val Ala
        115             120             125

Pro Ser Asp Pro Ser Ile Val Ser Leu Ile Glu Glu Ser Ala Ile Ile
    130             135             140

Asn Ala Gly Ala Pro Glu Ile Val Pro Pro Ala His Gly Gly Phe Thr
145             150             155             160

Ile Thr Ser Ser Glu Thr Thr Thr Pro Ala Ile Leu Asp Val Ser Val
            165             170             175

Thr Ser His Thr Thr Thr Ser Ile Phe Arg Asn Pro Val Phe Thr Glu
            180             185             190

Pro Ser Val Thr Gln Pro Gln Pro Pro Val Glu Ala Asn Gly His Ile
        195             200             205

FIG. 2B

Leu Ile Ser Ala Pro Thr Ile Thr Ser His Pro Ile Glu Glu Ile Pro
    210                    215                  220

Leu Asp Thr Phe Val Ile Ser Ser Ser Asp Ser Gly Pro Thr Ser Ser
225                  230                235              240

Thr Pro Val Pro Gly Thr Ala Pro Arg Pro Arg Val Gly Leu Tyr Ser
              245              250              255

Arg Ala Leu His Gln Val Gln Val Thr Asp Pro Ala Phe Leu Ser Thr
            260              265              270

Pro Gln Arg Leu Ile Thr Tyr Asp Asn Pro Val Tyr Glu Gly Glu Asp
       275             280              285

Val Ser Val Gln Phe Ser His Asp Ser Ile His Asn Ala Pro Asp Glu
    290              295              300

Ala Phe Met Asp Ile Ile Arg Leu His Arg Pro Ala Ile Ala Ser Arg
305                310              315              320

Arg Gly Leu Val Arg Tyr Ser Arg Ile Gly Gln Arg Gly Ser Met His
              325              330              335

Thr Arg Ser Gly Lys His Ile Gly Ala Arg Ile His Tyr Phe Tyr Asp
            340              345            350

Ile Ser Pro Ile Ala Gln Ala Ala Glu Glu Ile Glu Met His Pro Leu
       355             360              365

Val Ala Ala Gln Glu Asp Thr Phe Asp Ile Tyr Ala Lys Ser Phe Glu
    370              375              380

Pro Asp Ile Asn Pro Thr Gln His Pro Val Thr Asn Ile Ser Asp Thr
385                390              395              400

Tyr Leu Thr Ser Thr Pro Asn Thr Val Thr Gln Pro Trp Gly Asn Thr
            405              410            415

FIG. 2C

```
Thr Val Pro Leu Ser Ile Pro Asn Asp Leu Phe Leu Gln Ser Gly Pro
            420             425             430
Asp Ile Thr Phe Pro Thr Ala Pro Met Gly Thr Pro Phe Ser Pro Val
        435             440             445
Thr Pro Ala Leu Pro Thr Gly Pro Val Phe Ile Thr Gly Ser Gly Phe
    450             455             460
Tyr Leu His Pro Ala Trp Tyr Phe Ala Arg Lys Arg Arg Lys Arg Ile
465             470             475             480
Pro Leu Phe Phe Ser Asp Val Ala Ala Ser Met Ala Met His Gly Arg
            485             490             495
His Val Thr Leu Lys Asp Ile Val Leu Asp Leu Gln Pro Pro Asp Pro
            500             505             510
Val Gly Leu His Cys Tyr Glu Gln Leu Val Asp Ser Ser Glu Asp Glu
        515             520             525
Val Asp Glu Val Asp Gly Gln Asp Ser Gln Pro Leu Lys Gln His Tyr
    530             535             540
Gln Ile Val Thr Cys Cys Cys Gly Cys Asp Ser Asn Val Arg Leu Val
545             550             555             560
Val Gln Cys Thr Glu Thr Asp Ile Arg Glu Val Gln Gln Leu Leu Leu
            565             570             575
Gly Thr Leu Asn Ile Val Cys Pro Ile Cys Ala Pro Lys Thr Ala Ala
            580             585             590
Ala Leu Glu His His His His His  *
            595             600 601
```

FIG. 3

PROTEIN PURIFICATION

E. Coli CELL DISRUPTION
↓
INCLUSION BODY
PREPARATION
AND
SOLUBILISATION
↓
Q ANION EXCHANGER (POROS HQ50)
    300 mL (6cm x 10cm)
    Load 8.0M Urea, DTT, Tris pH 8.0
    Wash 8.0M Urea, DTT, Tris pH 7.5 50mM Salt
    Elute 8.0M Urea, DTT, Tris pH 7.5 350mM Salt
    Dilute 8x in Cation Load buffer
↓
S CATION EXCHANGER (POROS HS50)
    200 mL (6cm x 7cm)
    Load 8.0M Urea, DTT, Phosphate pH 6.2 50mM Salt
    Wash 8.0M Urea, DTT, Phosphate pH 6.2 210mM Salt
    Elute 8.0M Urea, DTT, Phosphate pH 6.2 500mM Salt
↓
SIZE EXCLUSION (PHARMACIA SUPERDEX 200)
    6,400mL (9cm x 100cm)
    Run buffer 8.0M Urea, DTT, Tris pH 8.0 75mM Salt
↓
Q ANION EXCHANGER (POROS HQ50)
CONCENTRATION
    60mL (5cm x 3.5cm)
    Load 8.0M Urea, DTT, Tris pH 8.0
    Wash 8.0M Urea, DTT, Tris pH 7.5
    Elute 8.0M Urea, DTT, Tris pH 7.5 350mM Salt
↓
SIZE EXCLUSION (PHARMACIA G25)
BUFFER EXCHANGE
UREA REMOVAL 5,955,087

POLYPEPTIDES USEFUL AS IMMUNOTHERAPEUTIC AGENTS AND METHODS OF POLYPEPTIDE PREPARATION

This application claims the benefit of priority under 35 USC 119(e) from copending provisional application 60/000, 034 filed Jun. 8, 1995.

FIELD OF THE INVENTION

The present invention relates to HPV polypeptide preparations and their use in prophylactic or therapeutic treatment of chronic HPV infection. Methods of preparing these combinations, including protein purification techniques and the engineering of nucleic acid sequences by recombinant DNA techniques in order to enhance and achieve high level expression of a particular protein in heterologous cells, in particular E. coli bacterial cells, are generally applicable in the field of protein production and form a further aspect of the invention.

BACKGROUND OF THE INVENTION, AND PRIOR ART

Human papillomaviruses (HPV) are agents responsible for several benign and malignant lesions which proliferate in the skin and mucosal surfaces of humans. They are a genetically diverse group of DNA viruses which infect epithelial tissue, and can cause a range of different human diseases. Over 60 different types of HPV have been distinguished, based on the extent of cross hybridisation between their genomes, and of those, different subgroups are associated primarily with different types of disease. For example HPVs of types 1, 2, etc are associated with cutaneous warts of the hands and feet. HPVs 5 and 8 are associated with the rare disorder epidermodysplasia verruciformis.

Approximately twenty HPV types infect the genital mucosa, and can be divided into two subsets on the basis of severity of the disease with which they are associated. The first group include viruses such as HPV-6 and HPV-11 which are associated with the majority of benign condylomas (warts), including genital warts. The second group includes HPVs 16, 18, 31, 33 and 45, associated with flat warts of the cervix, and involved in malignant conversions leading to carcinomas of the uterine cervix (zur Hausen, Cancer Res. 49 (1989) pp 4677–4681).

Diseases associated with HPC are generally characterised by benign proliferations of epithelial tissue (warts) caused directly by virus infection. The virus infects the basal non-keratinised cells of the epithelium but cannot complete is replication cycle in these cells. Instead virus gene expression is limited to a set of early proteins which can induce the infected cell to proliferate, giving rise to the characteristic wart. In the upper layers of the wart however, the infected cells begin to undergo terminal differentiation towards their final keratinised state, and this differentiation is sufficient to allow the virus to complete its replication cycle with the production of virus proteins and ultimately new virus particles.

These lesions, although proliferative, are at low risk of malignant conversion, and in most cases the warts remains benign. However, in some cases, over a period of years, cells carrying HPV sequences may become tumorigenic. In this case it appears that the bulk of the virus genome is likely to be lost, and a residual portion of the genome, usually including the virus E6 and E7 genes becomes integrated into the genome. This progression to malignant cancer is, however, associated primarily with a limited range of HPV types, namely HPVs 16, 18, 31, 33, 35, 45 and with particular tissues such as the cervix and penis.

It is known that the immune system can play a role in controlling HPV infection. It is well known that the incidence of HPV-induced skin warts and HPV-associated diseases increases in those who are receiving immunosuppressive treatment, suggesting that in many cases virus infection is kept under control by immunological mechanisms. Further evidence for the capacity of the immune system to control infection has come from study of spontaneous wart regression. A common observation is that in some individuals with genital warts, the warts suddenly disappear. Such regression warts have been studied histologically, revealing a substantial influx of T lymphocytes in the lesions. Regression is believed to be mediated by the immune system.

Effective immune responses to HPV infections are thought to be mainly cell-mediated since disease can persist in individuals with serum antibodies against HPV. Moreover, it is known that spontaneous regression of warts is often accompanied by lymphocytic infiltration, itching, reddening of the affected area and other symptoms characteristic of cell-mediated immune reaction. HPV infections are also common in patients with impaired cellular immunity, where persistence of viral disease suggests poor immune surveillance.

Studies on regression of papillomavirus-associated disease in vaccinated animal models also support the concept of an immune effector in combatting disease. For example, cattle vaccinated against Bovine papillomavirus (BPV) produced antibodies reported not to be neutralising, yet vaccination with a fusion protein comprising sequences of BPV L2 and non-HPV sequences (beta galactosidase) has been shown to produce both prophylactic and therapeutic responses in these animals: (see WO93/00436 of Cancer Research Campaign Technology Limited: Jarrett et al, and Jarrett et al. Virology, 184 (1991) pp 33–42).

The use of HPV proteins such as L1, L2 in the preparation of vaccines is known for example from WO 93/02184 (Univ of Queensland & CLS Ltd: I Frazer et al: Papilloma virus vaccine). Other HPV proteins have been described for use in immunodiagnostics, e.g. in WO 91/18294 (Medscand AB: J Dillner et al: Synthetic peptides of various human papillomaviruses, for diagnostic immunossay); and EP 0 375 555 (Medgeniz; G De Martynoff et al: Peptides, antibodies against them, and methods for detection and dosage of papilloma virus).

EP 0 456 197 (1991) (Behringwerke: C Bleul et al) discloses peptides with one or more seroreactive epitopes of defined sequence from HPV18 proteins E1, E6, and E7. EP 0 451 550 (1991) (Behringwerke: M Mueller et al) discloses peptides with one or more seroreactive epitopes of defined sequence from HPV16 proteins E4, E6, E7, or L1. The disclosures are for screening test purposes, and also mention vaccine use.

WO 93/00436 (Cancer Research Campaign Technology: WFH Jarrett et al) disclose papillomavirus proteins and fragments related to L2 protein for prophylaxis and therapy of papillomavirus tumours, also mentioning preparation of E7 protein.

WO 92/16636 (Immunology Ltd: MEG Boursnell et al) discloses genetic sequences of HPV16 and HPV18 E6 and E7 as fused genes inserted in a recombinant vaccinia virus vector, causing in-vivo expression of antigens after administration of the live virus vector.

WO 92/05248 (Bristol-Myers Squibb: EK Thomas et al) proposes materials for inhibiting and treating human papillomavirus infection and cell transformation, mentioning recombinant cells (including virus vectors) containing a gene encoding a peptide substantially corresponding to a region of the E6 and/or E7 gene product or a chimeric peptide compound of one or more regions of HPV proteins.

CP Crum et al, Virology 178 (1990) pp 238–246, describe expression of fused part-sequences of HPV-16 L1 and E4 and the use of the proteins with Freund's complete adjuvant to immunise rabbits to make antisera for diagnostic or other test purposes.

SUMMARY AND DESCRIPTION OF THE INVENTION

The present invention provides fusion polypeptides and aggregates of polypeptides having papillomavirus-derived antigens as described more particularly below, and compositions thereof and their use for immunogenic and vaccine purposes in eliciting papillomavirus-specific immune responses.

Also provided are methods of producing, treating and and purifying such polypeptides and compositions, as described below.

According to the invention there are provided polypeptides and polypeptide compositions comprising an antigenic determinant of a papillomavirus protein, in aggregated form which when in solution or dispersion can pass through a sterilisation filter, or in amorphous aggregated form.

The invention also provides fusion polypeptides that combine papilloma-virus-derived antigens, e.g. from each of at least two different papillomavirus proteins, e.g. comprising (a) at least an antigenic determinant of a papillomavirus L2 protein, and (b) at least an antigenic determinant selected from E1, E2, E4, E5, E6 and E7 papillomavirus proteins and L2 papillomavirus proteins of different papillomavirus type than in (a). Further fusion polypeptides provided hereby comprise antigenic determinants from at least two papillomavirus proteins selected from E1, E2,E4, E5, E6 and E7 papillomavirus proteins e.g. where the said proteins are from different papillomavirus types.

Particularly preferred polypeptides and compositions hereof comprise antigenic determinants of human papillomavirus proteins, e.g. of HPV type 6, 11, 16, 18. Antigenic determinants of proteins from other HPV types and proteins of non-human animal papillomaviruses can also be made and used.

In further detail, the invention provides for example polypeptides comprising antigenic determinants from each of at least two different HPV proteins. An antigenic determinant of a papillomavirus protein can for example be represented and provided in connection with the invention either by the full sequence of the papillomavirus protein concerned, or by such sub-sequences as may be desired, e.g. a sequence fragment comprising at least 25%, e.g. at least 50% or 75% of the full sequence of the protein concerned, e.g. a N-terminal or C-terminal sequence fragment. Sequences can be taken from clinical papillomavirus isolates or published sequences or muteins thereof.

The HPV proteins, of which antigenic determinants can form part of such a fusion polypeptide, can be selected for example from the L1, L2, E1, E2, E4, E5, E6 and E7 proteins. Proteins of for example (human) papillomavirus types HPV 6, 11, 16 and 18, as well as from other human or animal papillomavirus types can be used. Thus antigenic determinants of at least two papillomavirus proteins can for example be L2 and another, and/or E7 and another.

In particular examples, the polypeptide can comprise at least an antigenic determinant from each of at least two different papillomavirus proteins, and from the same or from different papillomavirus types. For example, at least one of the proteins can be selected from L1 or L2 and/or at least one of the proteins can be selected from E1, E2, E4, E5, E6 and E7.

In particular examples the invention provides a polypeptide comprising an antigenic determinant of HPV L2 protein and an antigenic determinant of HPV E7 protein, suitably comprising for example a substantially full length L2 and/or E7 protein of HPV, or antigenic fragments or muteins thereof.

A fusion protein comprising L2 and E7 proteins of HPV, can comprise a sequence fragment of at least 50% of the full sequence of each of L2 protein and E7 protein, e.g. substantially the full sequence of L2 and of E7: optionally further including a sequence of L1 protein.

The polypeptide may further include antigenic determinants of other HPV proteins or be in admixture or aggregated with other HPV proteins or protein fragments, such as L1 or another member or members of the L or E series of papillomavirus-encoded proteins.

The polypeptide can comprise a single protein consisting of a fusion of L2 and E7 or a fusion of L2, E7 and L1. Alternatively the polypeptide can comprise an L2-E7 fusion combined with L1 protein for prophylactic or therapeutic application.

The polypeptide may comprise a fusion molecule or can be derived from individual polypeptides coupled or aggregated together. Soluble or solubilised forms of the polypeptide fall within the scope of the invention.

In certain embodiments the polypeptide can be coupled by chemical crosslinking, in per se known manner, e.g. by standard techniques involving covalent attachment for example to exposed tyrosine residues or to the epsilon-amino groups of lysine residues or the carboxyl groups of aspartate and glutamate residues. Preferred embodiments are however fusion proteins each resulting from expression in a recombinant host cell of a polynucleotide sequence of which part encodes part of all of the amino acid sequence of a first papillomavirus protein and another part encodes part or all of the amino acid sequence of a second papillomavirus protein.

In particular, the invention provides for example a polypeptide comprising an antigenic determinant from each of at least two different papillomavirus proteins, in an aggregated form which when in solution or dispersion can pass through a sterilisation filter, e.g. a filter with pore size in the range 0.16–0.22 micron, e.g. 0.2 micron.

It can be seen that the invention provides for example a polypeptide comprising an antigenic determinant from each of at least two different papillomavirus proteins, e.g. L2 or L1 and at least one other of L1, L2, E1, E2, E4, E6 and E7, in a reaggregated form that when in solution or dispersion can pass through a sterilisation filter, e.g. a filter with a pore size in the range 0.16–0.22 micron, e.g. 0.2 micron.

Suitable forms of preparation can result for example by denaturation, or denaturation with reduction, e.g. with subsequent reaggregation of a polypeptide which can be a fusion protein or other papillomavirus protein, e.g. a single papillomavirus protein, expressed in the form of inclusion bodies in a recombinant host cell. Such a form can offer an advantage in that it can be relatively easily purified, e.g. for vaccine use.

Alternative aggregated preparations of the polypeptides need not be filterable to sterilise them and can be prepared and purified by aseptic technique.

Aggregated or reaggregated polypeptides as described herein can have for example masses in the range about 100,000 e.g. 160,000 to 10,000,000 dalton. The molecular weight of a dimer of L2E7 can be about 130,000. The aggregates can for example have diameters on electron microscopy in the range about 4 to 50 nm, e.g. 10 to 15 nm.

An example of a polypeptide provided by the invention as described in detail in the example below contains a reaggregated L2E7 fusion polypeptide containing aggregates of about 500,000 dalton, about 10–15 or 15–20 nm in diameter upon electron microscopy, with about 7–10, e.g. about 8 L2E7 fusion polypeptide chains per aggregate. More generally, the product can have about 2 to 200, e.g. 5–50 chains per aggregate particle, and the preparations of aggregate can comprise particles with a range of particle sizes within the composition.

Suitable reaggregation is obtainable for example as a result of slow or gradual removal of urea and thiol-reducing agent (often e.g. dithiothreitol, or other acceptable thiol-reducing agent such as gluthathione) from a denatured and reduced preparation of the fusion polypeptide in urea (e.g. about 8M urea) and thiol-reducing agent e.g. about 10 mM dithiothreitol (preferably lowered to about 0.1 mM or less, e.g. about 0.04 mM or less in the reaggregated product). Such gradual removal can for example result from the column chromatography procedure described in detail below. The denatured and reduced preparation of the fusion polypeptide is obtainable for example by solubilising, in urea and thiol-reducing agent, initially-insoluble inclusion bodies as produced by expression of the polypeptides in a $E.$ $coli$ T7 system.

Such aggregated soluble or disperse products are often amorphous, can lack L1 protein, and are otherwise distinct from virus-like particles based on papillomavirus L1 protein (and sometimes including other papillomavirus proteins), as reported to result from expression of HPV genes (including L1) in systems such as e.g. recombinant baculoviruses in insect cells or in yeast cells. For example, the virus-like particles have not been disclosed as having undertone solubilising denaturation and thiol-reduction followed by reaggregation.

The polypeptides mentioned above can suitably be prepared using recombinant DNA techniques. Thus the invention also provides nucleic acids which encode the above mentioned polypeptides, cloning and expression vectors incorporating them and parts of them, and transfected and transduced host cells incorporating such nucleic acids and able to express them as protein. In a preferred example, the nucleic acid comprises a fusion gene comprising for example the L2 and E7 genes isolated for example from an isolate of HPV-6 obtained from a clinical specimen of genital wart.

Preferably the polypeptides described above are prepared by expression of the nucleic acid in a prokaryotic or eukaryotic host using recombinant DNA techniques.

Specifically, a nucleic acid which encodes the desired polypeptide is incorporated into a suitable vector system as a suitable open reading frame with any accessory sequences proper for its expression in a chosen system. The host cell is transformed with the vector. Transformed host cells are then cultured and the desired polypeptide isolated from the culture, either from the supernatant or from the cells, as in examples given below. The above-mentioned vectors as well as transformed host cells form a further aspect of the invention.

Expression of polypeptides provided by the invention has been examined in yeast and baculovirus expression systems, which have been previously reported to allow expression of HPV-derived genes. It was found that in both cases it was possible to obtain expression of a full-length molecule, but that expression levels were sometimes low. It is presently preferred, for the sake of optimising expression levels, to use a prokaryotic host expression system (particularly a $E.$ $coli$ T7 system), rather than the two tested eukaryotic systems (yeast or baculovirus).

Immunogenic polypeptides and vaccine compositions provided hereby are useful in eliciting HPV-specific immune responses e.g. as vaccines for prophylaxis or therapy of papillomavirus-associated conditions. The immunogens, e.g. immuno-therapeutic or prophylactic vaccines for use in the prophylaxis or treatment of HPV-associated diseases can be used to generate immune responses, e.g. responses involving cellular immunity capable of mediating the regression of chronic HPV infections including genital warts (especially where the products and the infections are based on HPV of types 6 and/or 11) or cervical intra-epithelial neoplasia (especially where the products and the infections are based on HPV of types 16 and/or 18) in infected patients. Such immune response can be targeted towards T-cells, e.g. CD4+ cells, e.g. by the use of appropriate adjuvants.

Thus the invention further provides a method for preventing or treating HPV infection or lesions associated therewith, which method comprises administering to a patient an effective amount of a polypeptide as described herein.

Embodiments provided by the invention include vaccine preparations based on polypeptides as mentioned herein, which according to specificity are intended for use in eliciting immune responses to papillomavirus, particularly for example of papillomaviruses of types HPV 6 and 11, and of types HPV 16 and 18, for use in prophylaxis and therapy of human genital warts and of cervical intra-epithelial neoplasia.

Cross-reactivity between HPV's of different types has been observed, and according to such observable cross-reactivity the polypeptides and vaccines produced hereby can be used in eliciting useful immune responses against papillomavirus types other than the types from which they were derived.

The invention provides immunogenic compositions of the polypeptides mentioned above, suitable for administration by injection, comprising a carrier such as an immunological adjuvant. In certain preferred examples the adjuvant comprises aluminum hydroxide and/or monophosphoryl lipid A as described more particularly below.

Such immunogenic compositions, e.g. for use as a therapeutic or prophylactic vaccine in humans or non-human animals, can comprise an adsorption complex comprising "alum" (i.e. aluminium hydroxide usually Alhydrogel(TM) or Rehydrogel(TM) as conventionally used as vaccine adjuvant) having adsorbed thereon a polypeptide obtainable as mentioned above. The adsorption complex can be a binary complex consisting of the alum and the polypeptide, or there may be further constituents, e.g. MPL as described below, making for example a ternary complex of MPL, alum and polypeptide.

The polypeptide, either soluble or aggregated, may be used as vaccine directly or may be administered as a pharmaceutical composition comprising also a pharmaceutically acceptable vehicle, buffer, adjuvant or other acceptable material. Hence the invention further provides a vaccine or pharmaceutical composition which comprises a polypeptide as described above in combination with a suitable carrier or excipient.

The polypeptide can be either a soluble monomer, for example of L2E7, or a polypeptide aggregate. Preferably the polypeptide, e.g. an L2E7 fusion protein, is formulated by combining with an adjuvant or other accessory substance such as an immunostimulatory molecule in order to enhance its effect as a therapeutic antigen, and also to stimulate a preferred type of immune response in the recipient patient. Useful adjuvants include, but are not limited to: aluminium hydroxide ("alum"), e.g. in the form of Alhydrogel(TM) or Rehydrogel(TM); 3D-MPL (3-deacylated monophosphoryl lipid A) e.g. as described in U.S. Pat. No. 4,912,094 (Ribi Immunochem Research: KR Myers and AT Truchot: describing adjuvants based on modified lipopoly-saccharide, de-3-0-acy monophosphoryl lipid A), which can be applied for example as described in U.S. Pat. No. 4,912,094 or as in specification WO 94/21292 (Smithkline Beecham: P Hauser et al: Vaccine compositions containing 3-0-deacylated monophosphoryl Lipid A). Where both alum and MPL are used, the protein is preferably adsorbed first to alum and MPL added afterwards. Also usable are trehalose diesters such as trehalose dimycolate; saponins and their derivatives such as Quil A or QS-21, as for example described in specifications WO 88/09336 (Cambridge Bioscience: C A Kensil et al: Saponin adjuvant) and WO 93/05789 (Cambridge Biotech: C A Kensil et al: Saponin-antigen conjugates): ISCOMS or ISCOM matrices, as for example described in specifications WO 90/03184 (B Morein et al: Iscom matrix with immunomodulating activity, comprising lipid and optionally also adjuvants) and WO 92/21331 (Kabi Pharmacia AB: B Morein et al: Pharmaceutical carriers comprising sterol and saponin); or muramyl dipeptide, or cholera toxin B. Further accessory or immunostimulatory molecules useful in this connection include cytokines, such as interleukins, including but not limited to GM-CSF, IL-3, IL-2, IL-12 and IL-7. Such adjuvants and/or other accessory substances, can be used separately or in combination as desired.

Pharmaceutical compositions such as vaccines provided hereby can e.g. be: emulsified in acceptable mineral or hydrocarbon oil, including but not limited to squalene, or biodegradable mineral oils as described in specifications WO 91/00106 and WO 91/00107 (SEPPIC: B Brancq et al: describing injectable multi-phase emulsions and emulsion vectors with continuous oily phase); or encapsulated, e.g. by encapsulation in biodegradable microparticles or liposomes or nonionic surfactant vesicles: for these techniques see respectively e.g. specifications WO 94/27718 (DT O'Hagan et al: microparticles containing entrapped antigens and their use in immunization) and WO 93/19781 (PCT/GB93/00716) Preteus Molecular Design: J Alexander et al: Vaccines containing non-ionic surfactant vesicles with entrapped antigen).

The polypeptides may be given for therapeutic or prophylactic purposes. Routes and procedures of administration include, but are not limited to standard intramuscular, subcutaneous, intradermal, intravenous, oral or rectal routes and procedures.

The amount of polypeptide administered can be chosen according to the formulation and the condition to be treated. Generally it is expected that doses will be between 1–2000 $\mu$g of the protein, preferably 10–300 $\mu$g, e.g. 10–250 $\mu$g. Optimal amounts can readily be determined in subjects. One or more doses of the vaccine may be administered at intervals (see e.g. Example 13). This regime can readily be optimised in subjects.

Alternatively, a nucleic acid encoding said polypeptide can be incorporated into a suitable recombinant virus vector and introduced into a host organism, such as a human, in order that expression of the nucleic acid can give rise to the polypeptide in situ. Examples of viruses suitable for use as basis of recombinant virus vectors in this way are for example viruses as described in WO 92/05263 (Immunology Ltd: SC Inglis et al) and WO 92/16636 (Immunology Ltd: MEG Boursnell et al).

Vaccines containing HPV-related polypeptides as described herein may activate broad HPV-specific immune responses. Such immune responses can include: specific antibody, including HPV6 and HPV11 neutralising antibodies, cell mediated immunity including HPV6 and HPV11 specific lymphoproliferative responses, delayed type hypersensitivity responses, cytotoxic T cells, and cytokine production.

In the course of preparing a suitable vector for expression of the polypeptide of the invention, the applicants have arranged a technique which can enhance and achieve high level expression of a particular polypeptide in heterologous cells, in particular *E. coli* bacterial cells.

Thus in a further aspect the invention provides a method for preparing a recombinant polypeptide which method comprises expressing in a bacterial cell a nucleic acid sequence which encodes the desired polypeptide but which has been mutated such that codons or groups of codons which cause premature termination of transcription or translation have been replaced by degenerate codons.

In particular, applicants have found that in the T7 expression system of *E. coli*, the incidence of premature termination of transcription or translation can effectively be prevented or reduced by removal of at least one poly-T sequence such as [TTT]n where n is 2 or more, e.g. by replacing such a sequence with an acceptable alternative, e.g. a [TTC]n sequence which encodes the same amino acids, leading to higher yield of desired polypeptide.

In bacterial expression systems such as the T7 system, recombinant polypeptides are found in insoluble aggregates or 'inclusion bodies' (IBs) within the cell. The applicants have arranged a improved technique for the recovery of said recombinant polypeptides.

Thus in a further aspect of the invention there is provided a method of recovering a recombinant polypeptide from an inclusion body within a prokaryotic host cell, said method comprising subjecting a suspension comprising said inclusion bodies along with unwanted material e.g. broken-cell debris to cross-flow filtration and recovering recombinant polypeptide from inclusion bodies separated therefrom. This technique has the combined effect of separating inclusion bodies present in a cell homogenate from other cell debris and at the same time washing them, hence providing a useful degree of purification.

In a preferred embodiment of this process, the separated inclusion bodies are subsequently solubilised in situ and the polypeptide is recovered from the solution. Examples of solubilising reagents include urea and mixtures of urea and dithiothreitol or other sulphydryl reducing agent, e.g. at about 8M–10M concentration.

It can be particularly convenient to carry out cross-flow filtration of a crude suspension resulting from disruption of host cells, containing a desired expressed polypeptide in the form of inclusion bodies, in two stages in the same filtration apparatus, a first stage in which the desired inclusion bodies are retained and washed in the filter retentate under non-solubilising conditions, and a second stage in which said inclusion bodies are contacted with a solubilising liquid and collected in a filtrate in such liquid (e.g. in 8–10M urea optionally with sulphydryl reducer such as dithiothreitol). Removal of the solubiliser, and re-aggregation, can usefully follow.

A particular example of a protein preparation of the invention would comprise a fusion protein comprising L2E7 proteins based on HPV-6. The protein is suitably expressed in E. coli cells, purified to homogeneity and then formulated with an adjuvant, for example alum. The preparation would be of use in treating genital warts and would be formulated so as to be in a form suitable for administration by parenteral injection to the recipient patient.

The invention is further described below by way of example with reference to the accompanying diagrammatic drawings in which:

FIG. 1 shows a nucleotide sequence for a vector expressing a HPV L2E7 fusion protein according to an embodiment of the invention;

FIGS. 1a and 1b show sequences of the vector that precede the start codon and follow the stop codon in the sequence of FIG. 1;

FIG. 2 shows a corresponding aminoacid sequence; and

FIG. 3 illustrates a protein purification procedure for use according to an embodiment of the invention in purifying the L2E7 fusion protein of FIGS. 1 and 2.

The applicants have isolated certain HPV genes, in particular the L1, L2 and E7 genes from the HPV-6 virus. The gene sequences have been used as described herein to construct gene fusions for expression of HPV-6 proteins to high level sin prokaryotic and eukaryotic systems.

For this purpose, plasmid vectors for the expression of the above-described polypeptides such as HPV-6, L2 and E7 as a single fusion protein in E. coli have been constructed.

Genes from the HPV-6 virus were amplified by Polymerase Chain Reaction (PCR) from a viral DNA sample prepared from a single clinical isolate of wart tissue infected with HPV-6. The genes isolated were used to construct a gene fusion cassette for the expression of HPV-6 derived protein in a heterologous system.

A number of modifications to the gene construct were made in order to improve the production process. Particularly useful modifications were as follows:

1. Introduction of a leader sequence ("pelB leader") at the N terminus of the encoded protein sequence in order to enhance the expression of the protein in E. coli cells (but not to direct the expression to the periplasma).
2. Introduction of a sequence ("His-Tag") at the C terminus of the encoded protein sequence in order to allow purification of the protein by metal chelation chromatography.
3. Mutation of stretches of thymidine residues to eradicate sequences implicated in the premature termination of transcription of the fusion gene. The mutation affects solely the DNA sequence of the gene construct, but does not effect the sequence of the encoded protein, since it involved the mutation of the degenerate third position in the codon.

Constructs were assayed by transcription and translation of the protein open reading frames, in vitro. In the case of the HPV-6 L2E7 fusion protein, both a full-length protein (80 kD) and a truncated protein product (70 kD) were seen when using an HPV-6 L2E7 gene fusion construct expressed in vitro, and this pattern was repeated in vivo. The appearance of a truncated form of the target protein was correlated with the presence in the HPV-6 L2 sequence of a long run of Thymidine (T) residues. A second T-rich region containing 6 thymidine residues was also identified. These regions were subjected to mutagensis, in vitro, using obligonucleotides which altered the DNA sequence but not the amino acid sequence of the HPV-6 L2 protein. The mutated HPV-6 L2E7 gene fusion was subcloned into a plasmid expression vector driving expression of cloned sequences from a bacteriophage T7 promoter (pET expression system, Novagen). The plasmid construct obtained, designated pGW53, chosen for HPV-6 L2E7 expression, encoded an upstream leader sequence, pelB, the HPV-6 L2E7 ORF's and a downstream sequence encoding 6 histidine residues (His Tag) "in frame" with the C-terminus of the HPV-6 fusion protein.

FIGS. 1–2:

The sequence data in FIGS. 1 and 2 indicate, without limitation, nucleotide and encoded aminoacid sequence of a preferred example of the L2E7 fusion protein produced by the techniques described herein, including an upstream leader and downstream tag sequence. The leader sequence as well as the tag sequence (aa 591–601) can be omitted if desired. FIGS. 1a and 1b show non-coding sequences in the preferred T7 expression vector, which precede the start codon and follow the stop codon in FIG. 1.

FIG. 2 shows the sequence of the preferred fusion protein of L2 and E7. In the DNA sequence of 1827 base pairs, locations 7 to 1812 (inclusive of stop codon) encode a L2E7 fusion protein and tags. The sequence regions corresponding to L2 and E7 in FIGS. 1–2 have been found to incorporate a few differences by comparison with published separate aminoacid sequences of L2 and E7. The differences are as follows (with reference first to an aminoacid residue in the sequence numbering of FIGS. 1–2 herein, and then to the (different) aminoacid in the corresponding position of the published sequence):

105 Gly was Gln in the published sequence; 215 Ile was Val; 230 Ile was Val; 373 Glu as Asp; 381 Lys was Glu; 386 Asp was Gly; 422 Ile was Leu; 544 Tyr was Phe.

In addition a few 'silent' differences were found in polynucleotide sequence, i.e. differences not leading to any difference in translated aminoacid sequence. These are believed to be without significance for the present invention. Two silent mutations from TTTTTT to TTCTTC, produced for reasons as discussed in the present text, are located at aminoacid positions 83-4 and 483-4.

A fusion protein expressed with precise correspondence with the published sequences, and incorporated in compositions as disclosed herein would be highly cross-reactive with the preferred L2E7 fusion protein shown in FIGS. 1 and 2 and would elicit equivalently similar or highly cross-reactive immune responses.

Also functionally similar would be L2E7 fusion proteins derived from the sequences of other clinical isolates of HPV: such further isolates from the clinical environment could possibly have discrepancies of sequence as compared with the sequences given here, but these are expected not to be significant to the performance of the invention. If desired, any discrepancies found in a particular clinical isolate could readily be eliminated e.g. by site-specific mutagenesis of the corresponding cloning vectors prepared therefrom.

The gene construct obtained as described herein was inserted in an expression system optimised for high level expression of heterologous proteins in E. coli cells. This expression system was based on the growth of E. coli cells to a significant density followed by induction of the T7 polymerase within the cells, which leads to the high level transcription of the gene construct.

The protein product which was then expressed and accumulated within inclusion bodies inside the E. coli cells. Following harvest of the cells, the protein was purified away from bacterial proteins, and prepared as a solubilised protein extract. This protein extract comprises a high molecular mass aggregate of protein molecules, which is soluble in an aqueous solution.

The purified protein thus obtained can be used to form the basis of a therapeutic antigen product in particular for the treatment of genital warts.

The following Examples and the sequence data given herein illustrate the invention but without intent to limit the scope of the present disclosure.

EXAMPLE 1

Amplification of Cloning of HPV-6 Genes

Viral DNA of the HPV type in the infected tissue was originally deduced by PCR using a method based on a modification of the method of Snijders et al., 1990, Journal of General Virology, 71: pp 173–191 with standard primers for HPV-6.

HPV-6 L1, L2 and E7 genes were amplified by Polymerase Chain Reaction (PCR) from a viral DNA sample prepared from a single clinical isolate (H26) selected as the basis for development of the therapeutic entity on the basis of the ease of isolation of genes. The identify of the clinical isolate is not important and any ordinary clinical isolate of HPV-6 would be practically equivalent even though not identical. Initial PCR was performed using Taq DNA polymerase. Oligonucleotide primers used in the PCR reactions encoded 24 nucleotides of exact homology to the gene sequence of interest as well as additional nucleotides where these encoded restriction enzyme sites or were added to maintain the reading frame between eventual gene fusions or to introduce stop codons in the final expression constructs. An example of the oligonucleotide used is as follows:

```
JPC08 CAGTGTCGACGGTCTTCGGTGCGCAGATGG
      GACA                        SEQ ID NO 1
```

Non-coding strand oligonucleotide primer for amplification of HPV 7 E7 gene and SalI site for directional cloning.

The single PCR products from the amplification reactions of the L1, L2 and E7 genes were used as template DNA in sequencing reactions to generate a consensus sequence for each of the three genes. The consensus DNA sequence was assumed to be an accurate reflection of the actual DNA sequences of the genes in the viral DNA extracts because it was a sequence generated from many individual template molecules.

The HPV-6 L2 gene was amplified by PCR from HPV-6 viral DNA as a single product of approximately 1400 bp. The product was purified from agarose and used as a template for DNA sequence analysis, and a consensus sequence for the amplified L2 gene was generated using oligonucleotide primers.

The purified L2 product was directly subcloned into the vector pGEM-T to create plasmid pGW12. The full DNA sequence of the subcloned L2 gene was generated from the pGW12 template DNA using the same oligonucleotide primers as for the consensus sequence. The DNA sequence of the cloned L2 gene was shown to be identical to that of the consensus. The HPV-6 E7 gene was amplified by PCR from HPV-6 viral DNA as a single product of approximately 300 bp. This was purified from agarose and used as template for DNA sequence analysis, and a consensus sequence for the amplified gene was generated using oligonucleotide primers.

The purified E7 PCR product was directly subcloned into the vector pGEM-T to create plasmid pGW04. The full DNA sequence of the subcloned E7 gene was generated from the pGW04 template using the same oligonucleotide primers as for the consensus sequence. The sequence of the cloned E7 gene was shown to be identical to that of the consensus.

The HPV-6 L1 gene was amplified by PCR from HPV-6 viral DNA as a single product of approximately 1500 bp. This was purified from agarose and used as a template for DNA sequence analysis, and a consensus sequence for the amplified gene was generated using oligonucleotide primers.

The purified L1 PCR product was directly subcloned into the vector pGEM-T to create plasmid pGW-A. The full DNA sequence of the subcloned L1 gene was generated from the pGW-A template using the same oligonucleotide primers as for the consensus sequence. The sequence of the cloned E7 gene was shown to be identical to that of the consensus.

PCR products were purified from agarose gels by binding to silica matrix and ligated to pGEM-T vector DNA. The products of these ligation reactions were used to transform *E. coli* DH5a cells. Recombinant clones were isolated and further screened for the correct HPV-6 gene inserts using a method based on PCR.

The DNA sequences of the cloned HPV-6 L2 and E7 genes were obtained and compared with the consensus sequence generated directly from the original PCR products. Clones whose sequences agreed with the consensus were used for the construction of recombinant protein expression cassettes.

EXAMPLE 2

Comparison of HPV-6 Sequences with EMBL Database

The consensus sequence was compared to that of closely related HPV types including HPV-11, HPV-16 and HPV-18 as well as the published sequence of HPV-6b from the European Molecular Biology Laboratory (EMBL) DNA database to ensure that the genes amplified were from an HPV-6 type virus.

Comparisons were made with the help of Lasergne Navigator software (DNAStar Inc.) using the EditSeq, SegMan, Megalign and Proteam programs. Comparisons were made at the DNA level and from the predicted amino acid sequences of the three genes.

This analysis indicated that the amplified L2, L1 and E7 genes were derived from an HPV-6type virus. The results demonstrate that although the gene sequence is highly conserved, a number of changes from the predicted sequence were observed.

Accordingly, it is considered that suitable constructs for use in this invention can be made on the basis of DNA from wild-type clinical HPV isolates.

EXAMPLE 3

Construction of Expression Cassette

The individual genes for L2 and E7 were assembled to generate the fusion molecule in the following manner: Both the L2 and E7 genes were cloned by PCR amplification to introduce novel N- and C-terminal restriction enzyme sites, whilst maintaining the integrity of the protein sequence. These genes sequences were then ligated together into a cloning vector, using standard recombinant DNA techniques, to create a L2E7 fusion gene, so that the open reading frames of the two sequences were maintained. The L2E7 fusion gene was constructed as follows.

The HPV-6 L2 gene was initially generated as a 1.1 kb PCR fragment flanked by BamHI and Nco I sites. This PCR fragment was sub-cloned into the pGEM-T cloning vector. Clones possessing the required insert were digested with the two enzymes in order to liberate the L2 gene, which was then purified by separation on an agarose gel followed by extraction onto glass milk. Similarly the HPV-6 E7 gene was generated as a 300 bp Nco I-Sal I fragment, sub-cloned into pGEM-T. These two gene fragments were ligated together to produce a 1.4 kb BamH I-Sal I DNA fragment which encoded an L2E7 fusion protein.

The resulting BamH I-Sal I DNA fragment was then ligated into a derivative of pET16b, a non-expressing cloning vector possessing kanamycin resistance. The resulting construct was named pGW48. The L2E7 gene fusion was subsequently transferred to an expressing pET vector in order to analyse the expression of the protein in E. coli.

Following analysis of the expression of the fusion gene in E. coli, mutation of the gene was performed as described to eliminate stretches of T residues, which were believed to be causing premature termination of transcription.

The L2E7 fusion gene was then modified by PCR to generate BamH I and Not I termini capable of allowing the insertion of the gene cassette into an expression vector containing an in frame pelB leader sequence at the 5' end and an in frame His Tag at the 3' end. The PCR fragment was cloned through the pGEM-T vector, and finally transferred to a pET vector derived from pET22b. This final construct was named pGW53.

Following assembly, the fusion construct was transferred to a series of prokaryotic expression vectors known as pET vectors. These well known vectors comprise strong bacteriophage T7 transcription and translation signals. Expression may then be induced by providing a source of T7 RNA polymerase in the host cell, under the control of the inducible lacUV5 promoter. Addition of the inducer, IPTG, then results in conversion of the cell's resources into target gene expression. Potentially the desired product can then comprise more than 50% of the total cell protein. Moreover, because the system is inducible, it can maintain the target gene sequence in a transcriptionally silent state prior to induction, allowing the expression of gene sequences which are potentially toxic to the host cell.

Addition of IPTG to a rapidly growing culture of cells transformed with the pET vector containing the target gene therefore leads to induction of the polymerase enzyme and concomitant expression of the cloned gene. The protein product may either be secreted, or in the case of these HPV gene products directed into inclusion bodies.

The cloning step was performed by the introduction of a Bgl II restriction enzyme site at each end of the gene fragment by PCR mutagenesis, using the following oligonucleotide:

NRW170 GTCGACAGATCTGGCACATAGTAGGG
       CCCGA                          SEQ ID NO 2

(Oligonucleotide for PCR cloning of HPV 6 L2E7 into pET vector. Introduction of BgIII site into N-terminus of HPV 6 L2. No methionine codon is required for fusion into pET leader sequence (pelB).

DNA sequencing followed. The L2E7 fusion gene was then ligated into the following vectors: pET11b, pET12b, pET16b and pET22b, which differ in the nature of their N-terminal and C-terminal sequences. The recombinant plasmids were then used to transform an appropriate host cell. HMS174, which contains the gene for T7 polymerase. Other host cells that differ in their stringency of suppressing basal expression are available and have been successfully used in this method.

EXAMPLE 4

Expression of L2E7 Construct in E. coli

Individual bacterial colonies were picked from the transformation plate and used to inoculate 2 ml aliquotes of 2YT medium. These aliquots were grown up for 2 hours, then used to inoculate a 12 ml culture of warmed medium, adjusting the volume of inoculum to provide a consistent number of bacteria as determined by measurement of optical density at 600 nm. These cultures were grown up until the optical density reached 0.6, at which point the cultures were split into two 5.0 ml aliquots. IPTG at the recommended concentration of 1.0 mM was added to one culture, and both cultures were incubated under identical conditions for 3 hours.

At the end of this period, the bacteria were transferred to ice and the optical density was measured. The bacterial cultures were harvested by centrifugation in a 15 ml Falcon tube for 10 minutes at 4,000 rpm. The supernatant was removed and the bacteria resuspended in TE at a final volume of 0.5 ml.

Analysis by SDS-PAGE was carried out as follows:

The sample was then added to an equal volume of reducing electrophoresis sample buffer, and heated at 100° C. for 10 minutes. 50 $\mu$l of sample was then loaded on a 5–15% polyacrylamide gel, and electrophoresed at 10 mA for 12 hours. The protein bands were visualised by staining in Coomassie Brilliant Blue in 10% acetic acid, 10% methanol for 30 minutes, followed by destaining. A major protein band of molecular weight 90 kD, corresponding to the full-length L2E7 protein, could be detected by staining the gel in Coomassie, in addition to at least one other band, of 80 kD, corresponding to a product of either proteolytic degradation or premature termination of transcription or translation.

Following modification of the gene sequence by site-directed mutagenesis as described e.g. in Example 6, the 80 kD band was no longer detectable following staining by Coomassie Blue, suggesting that the hypothesis of premature termination of transcription or translocation was correct.

Comparison of the amount of protein present on the gel with a known standard allowed an estimate of the level of expression within the bacteria. The levels appeared to be consistently within the range 10–30 mg/L.

For more detailed characterisation of the expressed protein products, the gel was subjected to Western transfer, followed by probing with anti-L2 antisera generated by immunisation of sheep with E. coli-derived L2 fusion protein. Western blotting allowed the visulisation of a large number of bands of molecular weight below that of the full-length species, presumably all of which are again generated by proteolytic degradation or premature termination of transcription or translation.

The initial SDS-PAGE analysis demonstrated the presence of a Coomassie-staining protein band with a size corresponding to that expected for the full-length L2E7 gene product. In addition, there were a number of other bands visible, which may correspond to either proteolytic fragments of L2E7 or to premature termination artifacts.

This was investigated by Western blotting, using either anti-L2 or anti-E7 anti-sera. The results confirmed that the major product was L2E7, and suggested that the minor bands were lacking C-terminal regions.

Further characterisation was performed by protein sequencing, which confirmed that the two major bands contained intact N-terminal sequences, including an uncleaved pelB leader sequence.

EXAMPLE 5

In Vitro Transcription and Translation

In order to characterise the products further the genes were analysed in a series of coupled in vitro transcription and translation experiments. This system uses an introduced T7 polymerase enzyme to generate an mRNA transcript from the cloned gene in the expression vector, which is then translated in vitro to generate a synthetic protein product. By incorporation of a radio-label into the protein product, its synthesis can be monitored using SDS-PAGE analysis.

In vitro transcription and translation revealed a similar pattern of protein synthesis to that found in the *E. coli* heterologous system. The L2E7 fusion protein consisted of two major bands of 80 kD and 70 kD, while the L1 product contained two major bands at 30 and 32 kD in addition to the presumed full length product of 60 kD.

DNA sequence analysis revealed that in both the sequences for L1 and L2 there were stretches of poly-T consisting of between seven and nine T residues, which appeared to coincide with the positions of prematurely terminated fragments of both the L1 and L2E7 molecules. It was suggested that these regions caused premature termination of either transcription or translation, most probably the former. This belief was supported by the observation of a poly-T tract in the terminator sequence for the T7 polymerase.

EXAMPLE 6

Mutagenesis of DNA Sequences

In order to eliminate potential termination artifacts, it was decided to mutate two stretches of T-rich regions. The codon TTT encodes the amino acid phenylalanine (Phe), for which an alternative codon (TTC) exists. It was therefore decided to replace the TTT codon by mutation to generate the sequence TTC, thereby maintaining the reading frame and the natural protein sequence. This was chosen so as to leave unaffected, in this example, the properties of the product, by leaving unchanged the protein sequence of the immunotherapeutic reagent. However, the mutation should increase yield of expressed protein product by minimising the level of artifacts due to premature ending of transcription or translation.

Mutation was performed by the PCR technique of gene overlap extension using oligonucleotides JCT61, JPC81 defined below, in which the natural DNA sequence is replaced by the mutant sequence in the relevant area.

The following oligonucleotides were employed in the mutagenesis:

JCT61 CCAACCCTCCGAAGAACACCCCCAAAC

SEQ ID NO 3 (Non-coding strand oligonucleotide primer for mutagenesis of HPV 6 L2 at DNA sequence positions 159 and 162 (TTTTTT to TTCTTC)).

JPC81 GATCAAATATTAAAATGGG-
GAAGTTTGGGGGTGTTCTTCGGAGGG

SEQ ID NO 4: (Coding strand oligonucleotide primer for HPV 6 L2 incorporating a mutagenesis of the sequence TTTTTT to TTCTTC at position 159 and 162. The oligonucleotide encodes an Ssp1 site AATATT.

A second site was also mutated by site-directed matagenesis using the following oligonucleotide:

JPC90 CGTATTCCCTTATTCTTCTCAGATGTG-
GCGGC SEQ ID No 5 (Coding strand oligonucleotide primer for HPV 6 L2 incorporating in vitro mutagenesis of the sequence at position 1359 and 1362)

The final gene product was then inserted in order to create a final expression vector designed as pGW53 and analysed by in vitro and in vivo expression.

EXAMPLE 7

Expression of Mutated Sequences

Following mutagenesis of the L2E7 construct the effect was monitored by in vitro and in vivo expression followed by SDS-PAGE analysis, and Western blot analysis where appropriate.

Initial experiments were performed to analyse the in vitro transcription and translation products of both mutated L2E7 and L1 genes.

The in vivo expression of the mutated L2E7 and the L1 gene were examined as before. Individual colonies were selected and grown up to an optical density of 0.6, at which point IPTG was used to induct half the culture; three hours post-induction the cells were harvested and aliquots prepared for analysis by SDS-PAGE. The expression cassette was found to be translated satisfactorily.

Both in vitro and in vivo experiments confirmed that matagenesis of the poly-T-regions leads to a diminution in the yield of prematurely terminated fragments of both L2E7 and L1, and an enhancement of the yield of full-length product. The net result was a diminution in the yield of the 70 kD product from expression of L2E7 and a loss of the 30–32 kD fragments from expression of L1.

It is therefore clear the mutation of the poly-T regions leads to an enhanced expression of the full-length species in this expression system. This result has not previously been described for a T7 polymerase-based expression system, and may have wide applications in other areas of expression work.

EXAMPLE 8

Protein production and purification process

Dedicated master and working cell banks of *E. coli* HMS174 cells containing the pGW53 plasmid and derived as described herein are laid down and stored at −80° C. For production an ampoule from the working cell bank is thawed and cultured in 2YT medium to an appropriate volume for fermenter inoculation. Fermentation scale can range form 1.3 L to 50 L and further scale up may be envisaged. Cells were cultured until cell density reaches a preset point (typically 0.3 g per L). At this point the culture is induced with IPTG after which the cells are harvested some 2 hours later. Yields of 24–50 mg L2E7 per g dry wt cells have been obtained on occasions using standard fermentation conditions. Cell disruption and protein purification are then carried out as indicated below and in FIG. 3 of the accompanying drawings.

Cell breakage is performed to release insoluble L2E7 stored as intracellular inclusion bodies (IB's). This is done using a hydraulic press which causes cell lysis by passing the cells through a narrow aperture under a pressure of 5000 psi. Lysis of approx 95% efficiency can be achieved by standard methods and is virtually complete after 3 passes.

*E. coli* cell lysate containing insoluble L2E7 in the form of inclusion bodies is centrifuged. The sedimented pellet, containing inclusion bodies and cell debris was resuspended in a buffer containing Triton X-100 detergent. In such tangential cross-flow filtration, which is a per-se standard technique carried out in commercially-obtainable "Filtron" (TM) apparatus, a flow of liquid or suspension to be ultra-filtered or filtered is passed across an ultrafiltration or filtration membrane under a transmembrane pressure sufficient to drive filtrate through the membrane. In the present embodiment, tangential cross-flow filtration is used to concentrate the inclusion body suspension against a 0.16 μm filter. Inclusion bodies are concentrated in the retentate and contaminants are removed in the filtrate. The concentrate is then diluted to reduce the Triton X-100 concentration, and concentrated again. Urea and DTT (dithiothreitol) are then added to a final concentration of 8M and 10 mM respectively, which solubilises the L2E7. Denatured, reduced L2E7 protein then passes through the 0.16μ filter into The L2E7 in denatured, reduced, filtered form is then purified using ion exchange chromatography. 8.0M urea solubilised L2E7 protein is first purified by anion exchange chromatography using conditions indicated in FIG. 3. Typically 1–2 g of the product are purified on a 250–350 mL column. Urea-solubilised L2E7 is loaded onto the anion exchange resin, and weakly bound contaminants removed by elution with 4 column volumes of Urea DTT Tris buffer (pH 8.0) containing 50 mM NaCl. Finally, L2E7 protein is eluted from the column using a maximum of 5 column volumes of urea DTT Tris buffer (pH 8.0) containing 350 mM salt. Flow rate throughout the step is about 5 ml $cm^{-2}$/minute.

The anion exchange chromatography peak product is loaded onto a cation exchanger. Typically 1–2 g of product are purified on about 250 ml of column material. Product is loaded onto the resin at 2.5 ml min $cm^{-1}$ which is then washed with 4 column volumes of 8.0M urea DTT phosphate (pH 6.2) containing 210 mM sodium chloride followed by L2E7 peak elution with wash buffer containing 500 mM sodium chloride into approximately 1.5 column volumes.

The cation exchanger peak product was loaded onto a size exclusion matrix (as indicated in FIG. 3) using a running buffer of 25 mM Tris pH 8.0 containing 75 mM sodium chloride. Typically 100 ml containing 200–400 mg of L2E7 is loaded (at 0.2 ml $cm^{-2}$/min) onto 6.5 L of matrix with a bed height of 100 cm. The peak corresponding to the major product and minor N terminal clipped fragments was peak cut at an approximate elution volume of 0.46 column volumes.

The size exclusion chromatography peak at this stage of the process is dilute, at an approximate concentration of 0.25–0.5 mg $ml^{-1}$. The product (1–2 L) is concentrated by loading onto a small volume of anion exchange matrix (~75 ml) at a flow rate of 0.5 ml $cm^{-2}$/min. The product is eluted using urea DTT phosphate buffer pH 8.0 containing 1.0M sodium chloride. The peak volume is 1–2 column volumes.

The concentrated Q anion cartridge peak was buffer exchanged into a final formulation buffer at 48.9 mM Tris pH 8.0 containing 5 mM DTT. The column matrix is Sepharose medium G25 with a volume of ~2.5 liters. A 'slug' of buffer containing 8M urea equal to the product volume is preloaded onto the column. The product is then loaded at a ~100–150 mls load. The formulated buffer exchanged product peak is typically eluted at 0.5 column volumes using a flow rate of 0.06 ml $cm^{-2}$/min. The final product bulk is then –80° C. stored.

A solution or dispersion of the product L2E7 protein obtainable in this way is in an aggregated (reaggregated) form, which can nevertheless pass through a sterilising filter, e.g. a filter of gauge in the range 0.16–0.22 micron, e.g. 0.2 micron.

EXAMPLE 9

Cloning and Expression of HPV-6 Genes in Yeast—*Saccharomyces cerevisiae*

In order to examine the ability of other heterologous systems to express high levels of the HPV-6 genes, the genes for the L2E7 fusion construct and for L1 have been cloned into a generally available *S. cerevisiae* autonomously replicating expression vector. This vector, based on elements of the 2$\mu$ plasmid, allows expression of heterologous in-frames genes driven by the GAL7 promoter. The vector also contains the LEU-2d marker, for selection of increased copy numbers in yeast cells, and the kanamycin resistance gene enabling selection in *Escherichia coli*. The Saccharomyces host strain used for expression was S150-2B (genotype: a, leu2-3, 112, Δhis3, trpl-289, ura3-52).

Yeast were transformed with the HPV-6L2-E7 construct and grown up in medium containing 2% glucose as the sole carbon source, in order to repress transcription from the GAL7 promoter. Gene expression was induced in the presence of 2% galactose in the medium, as the sole carbon source.

Cell extracts were produced by disruption of the cell membranes in the presence of glass beads. The extraction buffer was Tris-based and contained a broad range protease inhibitors; PMSF, pepstatin, leupeptin, antipain and chymostatin. Cell extracts were processed by SDS PAGE and the resolved proteins were Western blotted using polyclonal antisera raised in sheep against HPV-6 L2 and HPV-6 E7.

Yields of HPV-6 L2-E7 fusion protein produced from Saccharomyces cerevisiae in this way have been estimated to be 10 $\mu$g per liter of culture in certain embodiments.

EXAMPLE 10

Cloning and Expression of HPV-6 Genes in Yeast—*Pichia pastoris*

An L2E7 fusion molecule (see Example 3 above) can be created as a BamH I—Not I DNA fragment, and cloned into a suitable expression vector such as a Pichia expression vector pPIC3K (obtained under license from Phillips Petroleum). The gene can be placed under the control of the Alcohol Oxidase promoter. AOXI, in order to allow high level expression of the fusion protein. Following linearisation of the expression construct, the DNA can be transfected into yeast cells by spheroplast fusion.

Transformants can be selected by their ability to grow in minimal media in the absence of histidine, unlike untransfected cells which retain the requirement for histidine in the growth medium. A second round of screening on the basis of slow growth on a methanol substrate can be performed to select for those clones containing an L2E7 gene integrated at the correct locus.

EXAMPLE 11

Cloning and Expression of HPV-6 Genes in Baculovirus

In order to investigate expression of the L2E7 fusion gene in baculovirus, two constructs were generated, each coding for an HPV-6 L2E7 fusion protein, either with or without a HisTag tail. Neither construct contained a leader sequence, as on this occasion it was wished to examine the level of intracellular expression.

The two constructs were cloned by PCR amplification, which introduced terminal Bgl II sites, into the pGEM-T vector. The L2E7 genes were then isolated as Bgl II-Bgl II fragments and subcloned into the BamHI cloning site of the transfer vector pBacPAK1 (Clontech). The orientation of the inserts were then determined by PCR analysis, and DNA was prepared from clones containing the correct orientation.

DNA from the pBacPAK1 transfer vector containing either L2E7 construct was transfected, using the standard lipofectin mediated procedure, into *Spodoptera frugiperda* (type S19) cells along with Bsu36 1 cut PBacPAK1 viral DNA (Clontech). In vivo homologous recombination between the plasmid and viral DNA then occurs to rescue the viral DNA, and in the process the target gene is transferred to the viral genome.

The progeny viruses generated in the co-transfection supernatant were then amplified by infecting fresh cells.

A fraction of the infected cells were harvested and genomic DNA was prepared. PCR amplification using the above primers indicated that recombinant virus was present in the cells.

The passage one virus stock was then used to further infect cells at a high multiplicity of infection to characterise gene expression by determining the time course of protein production: Confluent S19 cells in 6 well dishes were infected at a high multiplicity of infection, cells and supernatant were harvested 24 hrs, 48 hrs and 72 hrs post infection. The results of the experiment were observed by SDS-PAGE analysis and Western blotting in order to detect synthesis of the protein.

Recombinant protein was not observed on a Coomassie stained SDS/PAGE gel but was detected at low levels by Western blotting. As expected the protein was not secreted due to the absence of a leader sequence. The amplified genes were sequenced in full and subcloned into plasmid vectors. The gene sequences have been used to construct gene fusions for expression of HPV-6 proteins to high levels in prokaryotic and eukaryotic systems.

EXAMPLE 12

Immunogenicity of L2E7 in mice

The immunogenicity of an aggregate of L2E7 has been examined in mice. It was found that when an aggregate of L2E7 adsorbed onto aluminum hydroxide ('alum') was injected into B6CBA mice L2E7 specific immunity was elicited. This L2E7 specific immunity included serum antibodies, of immunoglobulin G (IgG) class and immunoglobulin G1 subclass (IgG1). L2E7 specific delayed type hypersensitivity responses and lymphoproliferative responses in vitro were also found.

The immunogenicity of L2E7 adsorbed onto alum was examined in B6CBA mice. Mice were given two subcutaneous injections of 180 $\mu$g L2E7/Alum 14 days apart.

Serum was collected 7, 14 and 56 days after the 2nd injection of L2E7/Alum. Serum anti-L2E7 antibody levels were determined in an L2E7 specific enzyme linked immunosorbent assay. Serum anti-L2E7 responses peaked 14 days after the 2nd injection of L2E7 (mid point titre 4.572 log10) and persisted to 56 days (mid point titre 4.127 log10).

In vivo delayed type hypersensitivity responses (DTH) to L2E7 were measured in a second group of mice immunized as above. 7 days after their 2nd injection with L2E7/Alum mice were challenged with 1.8 $\mu$g L2E7 in their right ear and an equal volume of buffer in their left ear. L2E7 specific increase in ear thickness were measured with an engineers micrometer 24, 48 & 72 hours after the ear challenge. Mice immunized with L2E7/Alum made in-vivo DTH responses.

In-vitro lymphoproliferative responses were measured with draining lymph node cells (axillary lymph node cells) taken from a third group of mice, seven days after their second injection with L2E7/alum product (as above). A single lymph node cell suspension was made and 2×10^6 viable lymphocytes/ml were plated out in medium (Iscove's modified Dulbecco's medium) supplemented with 1% normal mouse serum, glutamine, beta-mercaptoethanol and antibiotics. L2E7 was titrated into the cultures (from 91 micro-g/ml) and cell proliferation was assessed by incorporation of tritiated thymidine for the final 24 hours of the 72 hour culture. Lymph node cells from mice were immunized with L2E7/Alum proliferated in vitro in response to L2E7 (42000 cpm, stimulation index 50).

EXAMPLE 13

Immune responses in humans

A vaccine as described above, an aluminium hydroxide gel complex of L2E7 prepared equivalently as indicated above, has been shown to induce an appropriate dose-related immune response in healthy male volunteers. Cells from all of 36 vaccinated volunteers showed a L2E7-specific in-vitro lymphoproliferative response (CD4+ T cells) indicative of immune response to the product. The volunteers had been given the product by intramuscular injection in doses of 3, 30 or 300 $\mu$g, an initial dose at day 0 and repeated doses on day 7 and day 28 (accelerated schedule). (An alternative, slower, schedule for vaccination on days 0, 28 and 56 was also tried, and found less preferable.) Lymphoproliferative responses were seen from day 7 at dose levels including the lowest dose, 3 $\mu$g. L2E7 specific antibody response was also shown in 29 of 32 assessable samples from the volunteers (the three non-responders in the antibody test had been given the lowest dose). Increased in-vitro production of IL-5, consistent with the antibody production, was also seen. The two higher doses elicited T-cell proliferation sooner than the lowest dose. The highest dose, 300 $\mu$g, stimulated more IFN-gamma production than the lower doses. The observations made, of rapid T-cell proliferation and associated production of IFN-gamma, are appropriately consistent with the intended use of the product as a therapeutic vaccine for genital warts.

Regression of long-established human plantar warts, considered to be due to human papillomavirus, has been seen in a recipient of the product at a dose of 3 micro-g, whose cells were among those showing lymphoproliferative response. Regression was observable at day 7 and disappearance of warts occurred by day 14.

The invention described and the disclosure made herein are susceptible to many modifications and variations as will be apparent to, and readily performable by, the skilled reader in the light of this disclosure; and the disclosure extends to adaptations, combinations and subcombinations of the features mentioned and/or described herein. Documents cited herein are hereby incorporated by reference.

We claim:

1. An immunogenic composition suitable for administration by injection, which comprises the product of mixing an immunological adjuvant and a polypeptide or polypeptide composition comprising antigenic determinants of at least two papillomavirus proteins, wherein at least one antigenic determinant is of a papillomavirus L2 protein and at least one antigenic determinant is of a papillomavirus E1, E2, E4, E6 or E7 protein, in an amorphous reaggregated form which when in solution or dispersion can pass though a sterilization filter.

2. An immunogenic composition according to claim 1, comprising antigenic determinants of L2 and E7 proteins of HPV.

3. An immunogenic composition according to claim 2, comprising a sequence fragment of at least 50% of the full sequence of each of L2 protein and E7 protein.

4. An immunogenic composition according to claim 1, wherein the antigenic determinant is of a papillomavirus protein of HPV type 6, 11, 16, 18, or of a non-human animal papillomavirus.

5. An immunogenic composition according to claim 1, in the form of a denatured, reduced, and reaggregated preparation.

6. An immunogenic composition according to claim 1, obtainable by denaturation, or denaturation with reduction, and subsequent reaggregation of a polypeptide expressed in the form of inclusion bodies in a recombinant host cell.

7. An immunogenic composition according to claim 6, which has a molecular mass per aggregate in the range about 100,000 to about 10,000,000 dalton.

8. An immunogenic composition according to claim 6, which comprises aggregate particles with diameters on electron microscopy in the range of about 4 to 50 nm.

9. An immunogenic composition according to claim 5, which comprises aggregate particles having from 2–200 polypeptide chains per aggregate.

10. An immunogenic composition suitable for administration by injection, which comprises the product of mixing an immunological adjuvant and an amorphous aggregated preparation of a polypeptide or polypeptide composition comprising antigenic determinants of at least two papillomavirus proteins, said polypeptide comprising a fusion polypeptide comprising antigenic determinants selected from the following combinations: (i) at least an antigenic determinant of a first papillomavirus L2 protein together with at least an antigenic determinant selected from E1, E2, E4, E5, E6 and E7 papillomavirus proteins and L2 papillomavirus protein of different papillomavirus type than the type of the first papillomavirus protein; and (ii) at least one antigenic determinant from a first papillomavirus protein selected from E1, E2, E4, E5, E6, and E7 papillomavirus proteins of a first HPV type and at least one antigenic determinant from a second papillomavirus protein selected from E1, E2, E4, E5, E6 and E7 papillomavirus proteins of a second HPV type, where the said two proteins are from different papillomavirus types.

11. An immunogenic composition according to claim 10, comprising a fusion polypeptide comprising an antigenic determinant of L2 protein and an antigenic determinant from at least one of E1, E2, E4, E6 and E7 proteins.

12. An immunogenic composition according to claim 1 or 10, wherein the adjuvant comprises aluminum hydroxide and/or monophosphoryl lipid A.

13. A method of using an immunogenic composition according to claim 1 or 10 to produce a papillomavirus-specific immune response, which comprises administering said composition to a subject to be treated.

14. An immunogenic composition according to claim 6, which comprises aggregate particles with diameters on electron microscopy in the range of about 10–15 nm.

15. An immunogenic composition according to claim 5, which comprises aggregate particles having from 5–50 polypeptide chains per aggregate.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 1:

CAGTGTCGAC GGTCTTCGGT GCGCAGATGG GACA                               34

(2) INFORMATION FOR SEQ ID NO: 2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 2:

GTCGACAGAT CTGGCACATA GTAGGGCCCG A                                   31

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 3:

CCAACCCTCC GAAGAACACC CCCAAAC                                           27

(2) INFORMATION FOR SEQ ID NO: 4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 4:

GATCAAATAT TAAAATGGGG AAGTTTGGGG GTGTTCTTCG GAGGG                     45

(2) INFORMATION FOR SEQ ID NO: 5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 5:

CGTATTCCCT TATTCTTCTC AGATGTGGCG GC          32

(2) INFORMATION FOR SEQ ID NO: 6:

(i) SEQUENCE CHARACTERISTICS:
        (A) LENGTH: 1815 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (ix) FEATURE:
        (A) NAME/KEY: CDS
        (B) LOCATION: 7..1812

(xi) SEQUENCE DESCRIPTION: SEQ ID NO: 6:

```
ATACAT ATG AAA TAC CTG CTG CCG ACC GCT GCT GCT GGT CTG CTG CTC             48
       Met Lys Tyr Leu Leu Pro Thr Ala Ala Ala Gly Leu Leu Leu
         1               5                  10

CTC GCT GCC CAG CCG GCG ATG GCC ATG GAT ATC GGA ATT AAT TCG GAT             96
Leu Ala Ala Gln Pro Ala Met Ala Met Asp Ile Gly Ile Asn Ser Asp
 15                  20                  25                  30

CTG GCA CAT AGT AGG GCC CGA CGA CGC AAG CGT GCG TCA GCT ACA CAG            144
Leu Ala His Ser Arg Ala Arg Arg Arg Lys Arg Ala Ser Ala Thr Gln
                 35                  40                  45

CTA TAT CAA ACA TGT AAA CTC ACT GGA ACA TGC CCC CCA GAT GTA ATT            192
Leu Tyr Gln Thr Cys Lys Leu Thr Gly Thr Cys Pro Pro Asp Val Ile
             50                  55                  60

CCT AAG GTG GAA CAC AAC ACC ATT GCA GAT CAA ATA TTA AAA TGG GGG            240
Pro Lys Val Glu His Asn Thr Ile Ala Asp Gln Ile Leu Lys Trp Gly
         65                  70                  75

AGT TTG GGG GTG TTC TTC GGA GGG TTG GGT ATA GCC ACC GGT TCC GGC            288
Ser Leu Gly Val Phe Phe Gly Gly Leu Gly Ile Gly Thr Gly Ser Gly
     80                  85                  90

ACT GGG GGT CGT ACT GGC TAT GTT CCC TTA GGA ACT TCT GCA AAA CCT            336
Thr Gly Gly Arg Thr Gly Tyr Val Pro Leu Gly Thr Ser Ala Lys Pro
 95                 100                 105                 110

TCT ATT ACT AGT GGG CCT ATG GCT CGT CCT CCT GTG GTG GTG GAG CCT            384
Ser Ile Thr Ser Gly Pro Met Ala Arg Pro Pro Val Val Val Glu Pro
                115                 120                 125

GTG GCC CCT TCG GAT CCA TCC ATT GTG TCT TTA ATT GAA GAA TCG GCA            432
Val Ala Pro Ser Asp Pro Ser Ile Val Ser Leu Ile Glu Glu Ser Ala
            130                 135                 140

ATC ATT AAC GCA GGG GCG CCT GAA ATT GTG CCC CCT GCA CAC GGT GGG            480
Ile Ile Asn Ala Gly Ala Pro Glu Ile Val Pro Pro Ala His Gly Gly
        145                 150                 155

TTT ACA ATT ACA TCC TCT GAA ACA ACT ACC CCT GCA ATA TTG GAT GTA            528
Phe Thr Ile Thr Ser Ser Glu Thr Thr Thr Pro Ala Ile Leu Asp Val
160                 165                 170

TCA GTT ACT AGT CAT ACT ACT ACT AGT ATA TTT AGA AAT CCT GTC TTT            576
Ser Val Thr Ser His Thr Thr Thr Ser Ile Phe Arg Asn Pro Val Phe
175                 180                 185                 190

ACA GAA CCT TCT GTA ACA CAA CCC CAA CCA CCC GTG GAG GCT AAT GGA            624
Thr Glu Pro Ser Val Thr Gln Pro Gln Pro Pro Val Glu Ala Asn Gly
                195                 200                 205
```

-continued

| | |
|---|---|
| CAT ATA TTA ATT TCT GCA CCC ACT ATA ACG TCA CAC CCT ATA GAG GAA<br>His Ile Leu Ile Ser Ala Pro Thr Ile Thr Ser His Pro Ile Glu Glu<br>          210                    215                 220 | 672 |
| ATT CCT TTA GAT ACT TTT GTG ATA TCC TCT AGT GAT AGC GGT CCT ACA<br>Ile Pro Leu Asp Thr Phe Val Ile Ser Ser Ser Asp Ser Gly Pro Thr<br>             225                 230               235 | 720 |
| TCC AGT ACC CCT GTT CCT GGT ACT GCA CCT CGG CCT CGT GTG GGC CTA<br>Ser Ser Thr Pro Val Pro Gly Thr Ala Pro Arg Pro Arg Val Gly Leu<br>240                      245                 250 | 768 |
| TAT AGT CGT GCA TTG CAC CAG GTG CAG GTT ACA GAC CCT GCA TTT CTT<br>Tyr Ser Arg Ala Leu His Gln Val Gln Val Thr Asp Pro Ala Phe Leu<br>255                  260                 265            270 | 816 |
| TCC ACT CCT CAA CGC TTA ATT ACA TAT GAT AAC CCT GTA TAT GAA GGG<br>Ser Thr Pro Gln Arg Leu Ile Thr Tyr Asp Asn Pro Val Tyr Glu Gly<br>             275                 280               285 | 864 |
| GAG GAT GTT AGT GTA CAA TTT AGT CAT GAT TCT ATA CAC AAT GCA CCT<br>Glu Asp Val Ser Val Gln Phe Ser His Asp Ser Ile His Asn Ala Pro<br>          290                 295               300 | 912 |
| GAT GAG GCT TTT ATG GAC ATA ATT CGT TTG CAC AGA CCT GCT ATT GCG<br>Asp Glu Ala Phe Met Asp Ile Ile Arg Leu His Arg Pro Ala Ile Ala<br>          305                 310               315 | 960 |
| TCC CGA CGT GGC CTT GTG CGG TAC AGT CGC ATT GGA CAA CGG GGG TCT<br>Ser Arg Arg Gly Leu Val Arg Tyr Ser Arg Ile Gly Gln Arg Gly Ser<br>320                      325                 330 | 1008 |
| ATG CAC ACT CGC AGC GGA AAG CAC ATA GGG GCC CGC ATT CAT TAT TTT<br>Met His Thr Arg Ser Gly Lys His Ile Gly Ala Arg Ile His Tyr Phe<br>335                      340                 345            350 | 1056 |
| TAT GAT ATT TCA CCT ATT GCA CAA GCT GCA GAA GAA ATA GAA ATG CAC<br>Tyr Asp Ile Ser Pro Ile Ala Gln Ala Ala Glu Glu Ile Glu Met His<br>             355                 360               365 | 1104 |
| CCT CTT GTG GCT GCA CAG GAA GAT ACA TTT GAT ATT TAT GCT AAA TCT<br>Pro Leu Val Ala Ala Gln Glu Asp Thr Phe Asp Ile Tyr Ala Lys Ser<br>          370                 375               380 | 1152 |
| TTT GAA CCT GAC ATT AAC CCT ACC CAA CAC CCT GTT ACA AAT ATA TCA<br>Phe Glu Pro Asp Ile Asn Pro Thr Gln His Pro Val Thr Asn Ile Ser<br>          385                 390               395 | 1200 |
| GAT ACA TAT TTA ACT TCC ACA CCT AAT ACA GTT ACA CAA CCG TGG GGT<br>Asp Thr Tyr Leu Thr Ser Thr Pro Asn Thr Val Thr Gln Pro Trp Gly<br>400                      405                 410 | 1248 |
| AAC ACC ACA GTT CCA TTG TCA ATT CCT AAT GAC CTG TTT TTA CAG TCT<br>Asn Thr Thr Val Pro Leu Ser Ile Pro Asn Asp Leu Phe Leu Gln Ser<br>415                      420                 425            430 | 1296 |
| GGC CCT GAT ATA ACT TTT CCT ACT GCA CCT ATG GGA ACA CCC TTT AGT<br>Gly Pro Asp Ile Thr Phe Pro Thr Ala Pro Met Gly Thr Pro Phe Ser<br>             435                 440               445 | 1344 |
| CCT GTA ACT CCT GCT TTA CCT ACA GGC CCT GTT TTC ATT ACA GGT TCT<br>Pro Val Thr Pro Ala Leu Pro Thr Gly Pro Val Phe Ile Thr Gly Ser<br>          450                 455               460 | 1392 |
| GGA TTT TAT TTG CAT CCT GCA TGG TAT TTT GCA CGT AAA CGC CGT AAA<br>Gly Phe Tyr Leu His Pro Ala Trp Tyr Phe Ala Arg Lys Arg Arg Lys<br>             465                 470               475 | 1440 |
| CGT ATT CCC TTA TTC TTC TCA GAT GTG GCG GCC TCC ATG GCG ATG CAT<br>Arg Ile Pro Leu Phe Phe Ser Asp Val Ala Ala Ser Met Ala Met His<br>480                      485                 490 | 1488 |
| GGA AGA CAT GTT ACC CTA AAG GAT ATT GTA TTA GAC CTG CAA CCT CCA<br>Gly Arg His Val Thr Leu Lys Asp Ile Val Leu Asp Leu Gln Pro Pro<br>495                      500                 505            510 | 1536 |
| GAC CCT GTA GGG TTA CAT TGC TAT GAG CAA TTA GTA GAC AGC TCA GAA<br>Asp Pro Val Gly Leu His Cys Tyr Glu Gln Leu Val Asp Ser Ser Glu<br>             515                 520               525 | 1584 |

```
GAT GAG GTG GAC GAA GTG GAC GGA CAA GAT TCA CAA CCT TTA AAA CAA          1632
Asp Glu Val Asp Glu Val Asp Gly Gln Asp Ser Gln Pro Leu Lys Gln
            530                 535                 540

CAT TAC CAA ATA GTG ACC TGT TGC TGT GGA TGT GAC AGC AAC GTT CGA          1680
His Tyr Gln Ile Val Thr Cys Cys Cys Gly Cys Asp Ser Asn Val Arg
            545                 550                 555

CTG GTT GTG CAG TGT ACA GAA ACA GAC ATC AGA GAA GTG CAA CAG CTT         1728
Leu Val Val Gln Cys Thr Glu Thr Asp Ile Arg Glu Val Gln Gln Leu
            560                 565                 570

CTG TTG GGA ACA CTA AAC ATA GTG TGT CCC ATC TGC GCA CCG AAG ACC         1776
Leu Leu Gly Thr Leu Asn Ile Val Cys Pro Ile Cys Ala Pro Lys Thr
575                 580                 585                 590

GCG GCC GCA CTC GAG CAC CAC CAC CAC CAC CAC TGAGAT                      1815
Ala Ala Ala Leu Glu His His His His His His
                595                 600
```

(2) INFORMATION FOR SEQ ID NO: 7:

(i) SEQUENCE CHARACTERISTICS:
        (A) LENGTH: 601 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Lys Tyr Leu Leu Pro Thr Ala Ala Ala Gly Leu Leu Leu Leu Ala
 1               5                  10                  15

Ala Gln Pro Ala Met Ala Met Asp Ile Gly Ile Asn Ser Asp Leu Ala
            20                  25                  30

His Ser Arg Ala Arg Arg Lys Arg Ala Ser Ala Thr Gln Leu Tyr
            35                  40                  45

Gln Thr Cys Lys Leu Thr Gly Thr Cys Pro Pro Asp Val Ile Pro Lys
 50                  55                  60

Val Glu His Asn Thr Ile Ala Asp Gln Ile Leu Lys Trp Gly Ser Leu
 65                  70                  75                  80

Gly Val Phe Phe Gly Gly Leu Gly Ile Gly Thr Gly Ser Gly Thr Gly
                85                  90                  95

Gly Arg Thr Gly Tyr Val Pro Leu Gly Thr Ser Ala Lys Pro Ser Ile
            100                 105                 110

Thr Ser Gly Pro Met Ala Arg Pro Pro Val Val Glu Pro Val Ala
            115                 120                 125

Pro Ser Asp Pro Ser Ile Val Ser Leu Ile Glu Glu Ser Ala Ile Ile
130                 135                 140

Asn Ala Gly Ala Pro Glu Ile Val Pro Pro Ala His Gly Gly Phe Thr
145                 150                 155                 160

Ile Thr Ser Ser Glu Thr Thr Thr Pro Ala Ile Leu Asp Val Ser Val
                165                 170                 175

Thr Ser His Thr Thr Thr Ser Ile Phe Arg Asn Pro Val Phe Thr Glu
            180                 185                 190

Pro Ser Val Thr Gln Pro Gln Pro Pro Val Glu Ala Asn Gly His Ile
            195                 200                 205

Leu Ile Ser Ala Pro Thr Ile Thr Ser His Pro Ile Glu Glu Ile Pro
210                 215                 220

Leu Asp Thr Phe Val Ile Ser Ser Ser Asp Ser Gly Pro Thr Ser Ser
225                 230                 235                 240

Thr Pro Val Pro Gly Thr Ala Pro Arg Pro Arg Val Gly Leu Tyr Ser
                245                 250                 255
```

```
Arg Ala Leu His Gln Val Gln Val Thr Asp Pro Ala Phe Leu Ser Thr
            260                 265                 270

Pro Gln Arg Leu Ile Thr Tyr Asp Asn Pro Val Tyr Glu Gly Glu Asp
        275                 280                 285

Val Ser Val Gln Phe Ser His Asp Ser Ile His Asn Ala Pro Asp Glu
290                 295                 300

Ala Phe Met Asp Ile Ile Arg Leu His Arg Pro Ala Ile Ala Ser Arg
305                 310                 315                 320

Arg Gly Leu Val Arg Tyr Ser Arg Ile Gly Gln Arg Gly Ser Met His
                325                 330                 335

Thr Arg Ser Gly Lys His Ile Gly Ala Arg Ile His Tyr Phe Tyr Asp
            340                 345                 350

Ile Ser Pro Ile Ala Gln Ala Ala Glu Glu Ile Glu Met His Pro Leu
        355                 360                 365

Val Ala Ala Gln Glu Asp Thr Phe Asp Ile Tyr Ala Lys Ser Phe Glu
370                 375                 380

Pro Asp Ile Asn Pro Thr Gln His Pro Val Thr Asn Ile Ser Asp Thr
385                 390                 395                 400

Tyr Leu Thr Ser Thr Pro Asn Thr Val Thr Gln Pro Trp Gly Asn Thr
                405                 410                 415

Thr Val Pro Leu Ser Ile Pro Asn Asp Leu Phe Leu Gln Ser Gly Pro
            420                 425                 430

Asp Ile Thr Phe Pro Thr Ala Pro Met Gly Thr Pro Phe Ser Pro Val
        435                 440                 445

Thr Pro Ala Leu Pro Thr Gly Pro Val Phe Ile Thr Gly Ser Gly Phe
450                 455                 460

Tyr Leu His Pro Ala Trp Tyr Phe Ala Arg Lys Arg Arg Lys Arg Ile
465                 470                 475                 480

Pro Leu Phe Phe Ser Asp Val Ala Ala Ser Met Ala Met His Gly Arg
                485                 490                 495

His Val Thr Leu Lys Asp Ile Val Leu Asp Leu Gln Pro Pro Asp Pro
            500                 505                 510

Val Gly Leu His Cys Tyr Glu Gln Leu Val Asp Ser Ser Glu Asp Glu
        515                 520                 525

Val Asp Glu Val Asp Gly Gln Asp Ser Gln Pro Leu Lys Gln His Tyr
530                 535                 540

Gln Ile Val Thr Cys Cys Cys Gly Cys Asp Ser Asn Val Arg Leu Val
545                 550                 555                 560

Val Gln Cys Thr Glu Thr Asp Ile Arg Glu Val Gln Gln Leu Leu Leu
                565                 570                 575

Gly Thr Leu Asn Ile Val Cys Pro Ile Cys Ala Pro Lys Thr Ala Ala
            580                 585                 590

Ala Leu Glu His His His His His His
        595                 600

(2) INFORMATION FOR SEQ ID NO: 8:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 8:
```

```
AGATCTCGAT CCCGCGAAAT TAATACGACT CACTATAGGG GAATTGTGAG CGGATAACAA    60

TTCCCCTCTA GAAATAATTT TGTTTAACTT TAAGAAGGAG ATATACAT               108
```

(2) INFORMATION FOR SEQ ID NO: 9:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 9:

```
GATCCGGCTG CTAACAAAGC CCGAAAGGAA GCTGAGTTGG CTGCTGCCAC CGCTGAGCAA    60

TAACTAGCAT AACCCCTTGG GGCCTCTAAA CGGGTCTTGA GGGGTTTTTT G            111
```

(2) INFORMATION FOR SEQ ID NO: 10:

(i) SEQUENCE CHARACTERISTICS:
        (A) LENGTH: 601 amino acids
        (B) TYPE: amino acid
        (D) TOPOLOGY: linear (ii) MOLECULE TYPE: protein (iii) HYPOTHETICAL: NO (iii) ANTI-SENSE: NO (xi) SEQUENCE DESCRIPTION: SEQ ID NO: 10:

```
Met Lys Tyr Leu Leu Pro Thr Ala Ala Ala Gly Leu Leu Leu Leu Ala
1               5                   10                  15

Ala Gln Pro Ala Met Ala Met Asp Ile Gly Ile Asn Ser Asp Leu Ala
            20                  25                  30

His Ser Arg Ala Arg Arg Lys Arg Ala Ser Ala Thr Gln Leu Tyr
        35                  40                  45

Gln Thr Cys Lys Leu Thr Gly Thr Cys Pro Pro Asp Val Ile Pro Lys
    50                  55                  60

Val Glu His Asn Thr Ile Ala Asp Gln Ile Leu Lys Trp Gly Ser Leu
65                  70                  75                  80

Gly Val Phe Phe Gly Gly Leu Gly Ile Gly Thr Gly Ser Gly Thr Gly
                85                  90                  95

Gly Arg Thr Gly Tyr Val Pro Leu Gly Thr Ser Ala Lys Pro Ser Ile
            100                 105                 110

Thr Ser Gly Pro Met Ala Arg Pro Pro Val Val Val Glu Pro Val Ala
            115                 120                 125

Pro Ser Asp Pro Ser Ile Val Ser Leu Ile Glu Glu Ser Ala Ile Ile
    130                 135                 140

Asn Ala Gly Ala Pro Glu Ile Val Pro Ala His Gly Gly Phe Thr
145                 150                 155                 160

Ile Thr Ser Ser Glu Thr Thr Thr Pro Ala Ile Leu Asp Val Ser Val
                165                 170                 175

Thr Ser His Thr Thr Thr Ser Ile Phe Arg Asn Pro Val Phe Thr Glu
            180                 185                 190

Pro Ser Val Thr Gln Pro Gln Pro Pro Val Glu Ala Asn Gly His Ile
        195                 200                 205

Leu Ile Ser Ala Pro Thr Ile Thr Ser His Pro Ile Glu Glu Ile Pro
```

-continued

```
                    210                 215                 220
Leu Asp Thr Phe Val Ile Ser Ser Asp Ser Gly Pro Thr Ser Ser
225                 230                 235                 240

Thr Pro Val Pro Gly Thr Ala Pro Arg Pro Val Gly Leu Tyr Ser
                    245                 250                 255

Arg Ala Leu His Gln Val Gln Val Thr Asp Pro Ala Phe Leu Ser Thr
                260                 265                 270

Pro Gln Arg Leu Ile Thr Tyr Asp Asn Pro Val Tyr Glu Gly Glu Asp
            275                 280                 285

Val Ser Val Gln Phe Ser His Asp Ser Ile His Asn Ala Pro Asp Glu
        290                 295                 300

Ala Phe Met Asp Ile Ile Arg Leu His Arg Pro Ala Ile Ala Ser Arg
305                 310                 315                 320

Arg Gly Leu Val Arg Tyr Ser Arg Ile Gly Gln Arg Gly Ser Met His
                325                 330                 335

Thr Arg Ser Gly Lys His Ile Gly Ala Arg Ile His Tyr Phe Tyr Asp
                340                 345                 350

Ile Ser Pro Ile Ala Gln Ala Ala Glu Glu Ile Glu Met His Pro Leu
            355                 360                 365

Val Ala Ala Gln Glu Asp Thr Phe Asp Ile Tyr Ala Lys Ser Phe Glu
        370                 375                 380

Pro Asp Ile Asn Pro Thr Gln His Pro Val Thr Asn Ile Ser Asp Thr
385                 390                 395                 400

Tyr Leu Thr Ser Thr Pro Asn Thr Val Thr Gln Pro Trp Gly Asn Thr
                405                 410                 415

Thr Val Pro Leu Ser Ile Pro Asn Asp Leu Phe Leu Gln Ser Gly Pro
            420                 425                 430

Asp Ile Thr Phe Pro Thr Ala Pro Met Gly Thr Pro Phe Ser Pro Val
            435                 440                 445

Thr Pro Ala Leu Pro Thr Gly Pro Val Phe Ile Thr Gly Ser Gly Phe
        450                 455                 460

Tyr Leu His Pro Ala Trp Tyr Phe Ala Arg Lys Arg Arg Lys Arg Ile
465                 470                 475                 480

Pro Leu Phe Phe Ser Asp Val Ala Ala Ser Met Ala Met His Gly Arg
                485                 490                 495

His Val Thr Leu Lys Asp Ile Val Leu Asp Leu Gln Pro Pro Asp Pro
                500                 505                 510

Val Gly Leu His Cys Tyr Glu Gln Leu Val Asp Ser Ser Glu Asp Glu
            515                 520                 525

Val Asp Glu Val Asp Gly Gln Asp Ser Gln Pro Leu Lys Gln His Tyr
        530                 535                 540

Gln Ile Val Thr Cys Cys Gly Cys Asp Ser Asn Val Arg Leu Val
545                 550                 555                 560

Val Gln Cys Thr Glu Thr Asp Ile Arg Glu Val Gln Gln Leu Leu Leu
                565                 570                 575

Gly Thr Leu Asn Ile Val Cys Pro Ile Cys Ala Pro Lys Thr Ala Ala
                580                 585                 590

Ala Leu Glu His His His His His His
            595                 600
```